(12) United States Patent
Hodson

(10) Patent No.: US 8,540,196 B1
(45) Date of Patent: Sep. 24, 2013

(54) BREATHING HOSE SUPPORT SYSTEM

(76) Inventor: Ernest F. Hodson, Monroe, CT (US)

(*) Notice: Subject to any disclaimer, the term of this patent is extended or adjusted under 35 U.S.C. 154(b) by 938 days.

(21) Appl. No.: 12/331,473

(22) Filed: Dec. 10, 2008

Related U.S. Application Data

(63) Continuation-in-part of application No. 11/972,334, filed on Jan. 10, 2008, now abandoned.

(51) Int. Cl.
   *F16L 3/00* (2006.01)
(52) U.S. Cl.
   USPC ............... 248/121; 248/75; 248/80; 248/81; 248/124.1; 248/176.1
(58) Field of Classification Search
   USPC ............. 248/75, 80, 81, 176.1, 121, 124.1; 81/459, 57.4, 470.3
   See application file for complete search history.

(56) References Cited

U.S. PATENT DOCUMENTS

| | | | | |
|---|---|---|---|---|
| 2,718,886 A | * | 9/1955 | Sutton | 602/33 |
| 3,333,613 A | * | 8/1967 | Bosse | 81/57.4 |
| 3,658,284 A | * | 4/1972 | Haasl | 248/145 |
| 4,995,576 A | * | 2/1991 | Kieswetter | 248/145 |
| 5,109,736 A | * | 5/1992 | Dixon | 81/57.4 |

* cited by examiner

Primary Examiner — Amy J Sterling

(57) ABSTRACT

A breathing hose support system for efficiently supporting a supply hose and mask in a proper position while being worn by an individual. The breathing hose support system generally includes a base, wherein the base may be partially supported by a bed frame or comprised of a self supported configuration. A vertical support extends from the base and a rotator assembly extends from the vertical support opposite the base. A horizontal support extends from the rotator assembly and is able to rotate a predetermined amount along a substantially horizontal plane via the rotator assembly. The horizontal support may also include a plurality of carrier assemblies movably connected to the horizontal support, wherein the carrier assemblies travel along a longitudinal axis of the horizontal support. A plurality of hose supports also extend from the carrier assemblies, wherein the hose supports receive a supply hose and wherein the hose is able to freely move via functioning of the carrier assemblies and the rotator assembly.

9 Claims, 23 Drawing Sheets

BREATHING HOSE SUPPORT SYSTEM

CROSS REFERENCE TO RELATED APPLICATIONS

I hereby claim benefit under Title 35, United States Code, Section 120 of U.S. patent application Ser. No. 11/972,334 filed Jan. 10, 2008 now abandoned. This application is a continuation in-part of the Ser. No. 11/972,334 application. The 11/972,334 application is currently pending. The Ser. No. 11/972,334 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to supply hose stands and more specifically it relates to a breathing hose support system for efficiently supporting a supply hose and mask in a proper position while being worn by an individual.

2. Description of the Related Art

Any discussion of the related art throughout the specification should in no way be considered as an admission that such related art is widely known or forms part of common general knowledge in the field.

Often an individual with apnea or another breathing problem must wear a breathing mask. The breathing mask is generally made to form fit the face of the individual utilizing the mask and is fastened to the head of the individual by adjustable straps. Due to body movement during sleep or otherwise (i.e. walking around, etc.) the mask's seal with the face is often broken and the breathing supply is interrupted causing discomfort, loss of sleep, sleep deprivation which can lead to narcolepsy, an abrupt wakening, a heart attack or even death.

Some individuals elect not to wear a breathing mask, wherein they may find the masks uncomfortable to sleep in, and thus often times compromising their health for comfort. Because of the inherent problems with the related art, there is a need for a new and improved breathing hose support system for efficiently supporting a supply hose and mask in a proper position while being worn by an individual.

BRIEF SUMMARY OF THE INVENTION

The general purpose of the present invention is to provide a breathing hose support system that has many of the advantages of the supply hose stands mentioned heretofore. The invention generally relates to a supply hose stand which includes a vertical support, a rotator assembly extending from the vertical support, a rotator stop mechanically connected between the vertical support and the rotator assembly, wherein the rotator stop limits a horizontal rotation of the rotator assembly, a horizontal support extending from the rotator assembly, wherein the horizontal support rotates about the vertical support via the rotator assembly and at least one hose support extending from the horizontal support.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a breathing hose support system for efficiently supporting a supply hose and mask in a proper position while being worn by an individual.

Another object is to provide a breathing hose support system which eliminates the supply hose resistance and subsequent effects on the face mask.

Another object is to provide a breathing hose support system that attaches upon a bed frame.

Another object is to provide a breathing hose support system that adjusts to all bed sizes and sleeping arrangements.

An additional object is to provide a breathing hose support system that adjusts in various manners to accommodate individuals moving around in their sleep.

Another object is to provide a breathing hose support system that permits sitting or standing positions.

A further object is to provide a breathing hose support system that is portable.

Another object is to provide a breathing hose support system that includes a support table for breathing equipment adjacent to the bedside.

Another object is to provide a breathing hose support system that may be comprised of a self-supported structure.

Another object is to provide a breathing hose support system that can be easily broken down and converted to a side table.

An additional object is to provide a breathing hose support system that forces a supply line to maintain a position entering the face mask from above and to the side of the head rather than frontal which would inhibit movements such as sitting up or getting out of bed.

An additional object is to provide a breathing hose support system that effortlessly follows the movements of the user and returns to a preferred position with the inactivity of the user.

An additional object is to provide a breathing hose support system that allows the user the freedom and peace of mind to know that moving or turning is not going to dislocate the face mask and to have a provision to minimize the effects of quick extreme movements during sleep.

An additional object is to provide a breathing hose support system that allows for the hose to be adequately suspended allowing for the adjustment of hose lengths between supports and the face mask an effortless task.

An additional object is to provide a breathing hose support system that allows for mobility through wheels and may also attach to the bed frame for a more permanent structure.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
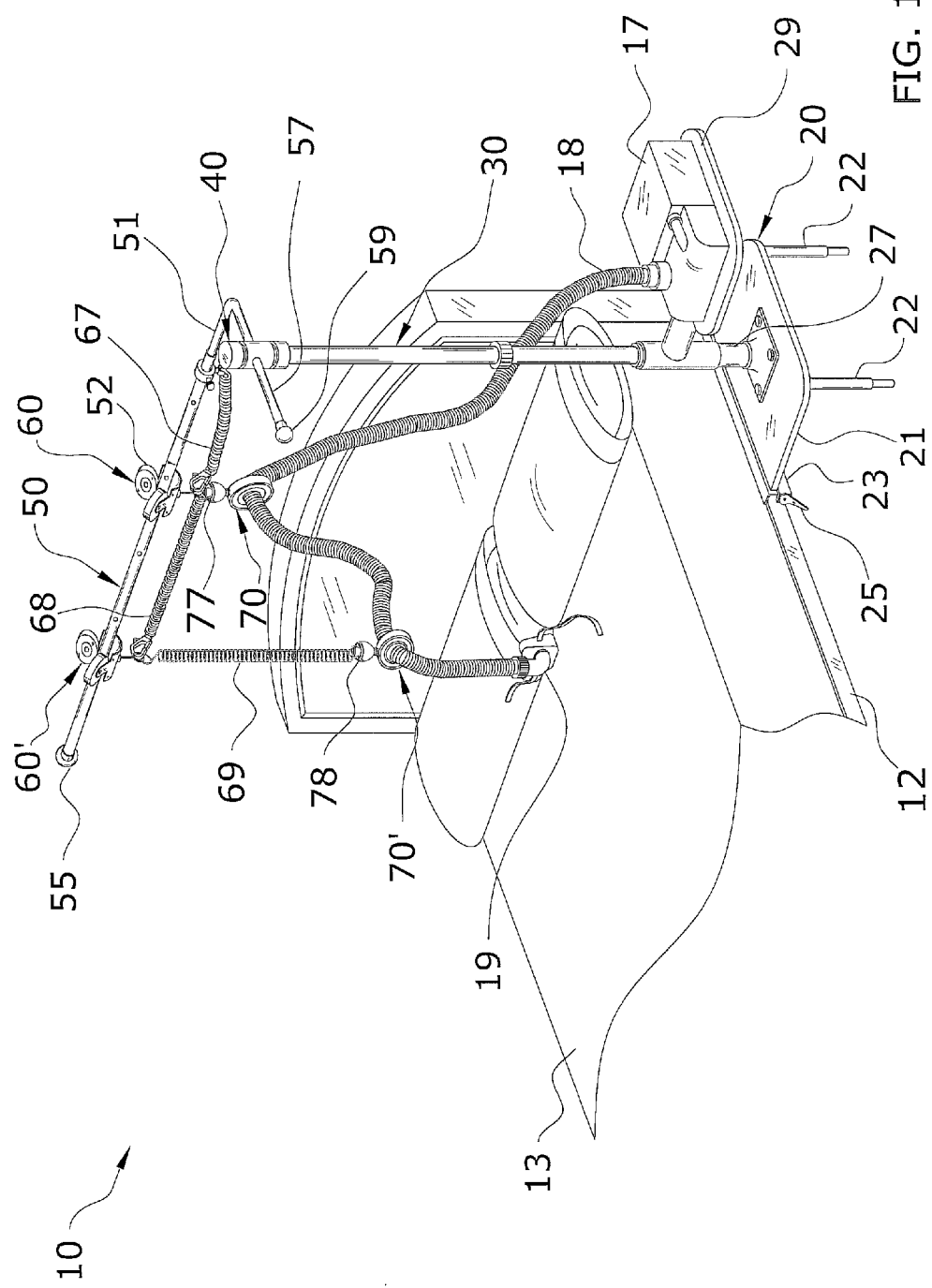
FIG. 1 is an upper perspective view of the present invention in use.

Turning now descriptively to the drawings, in which similar reference characters denote similar elements throughout the several views, FIGS. 1 through 23 illustrate a breathing hose support system 10, which comprises a base 20, wherein the base 20 may be partially supported by a bed frame 12 or comprised of a self supported configuration. A vertical support 30 extends from the base 20 and a rotator assembly 40 extends from the vertical support 30 opposite the base 20. A horizontal support 50 extends from the rotator assembly 40 and is able to rotate a predetermined amount along a substantially horizontal plane via the rotator assembly 40. The horizontal support 50 may also include a plurality of carrier assemblies 60, 60' movably connected to the horizontal support 50, wherein the carrier assemblies 60, 60' travel along a longitudinal axis of the horizontal support 50. A plurality of hose supports 70, 70' also extend from the carrier assemblies 60, 60', wherein the hose supports 70, 70' receive a supply hose 18 and wherein the hose 18 is able to freely move via functioning of the carrier assemblies 60, 60' and the rotator assembly 40.

The present invention is preferably utilized with a continuous positive airway pressure (CPAP) device and associate supply hose 18 for air, oxygen, etc. and face mask 19. It is appreciated however that the present invention may be utilized with various devices and for various purposes.

B. Base

Figure 14:
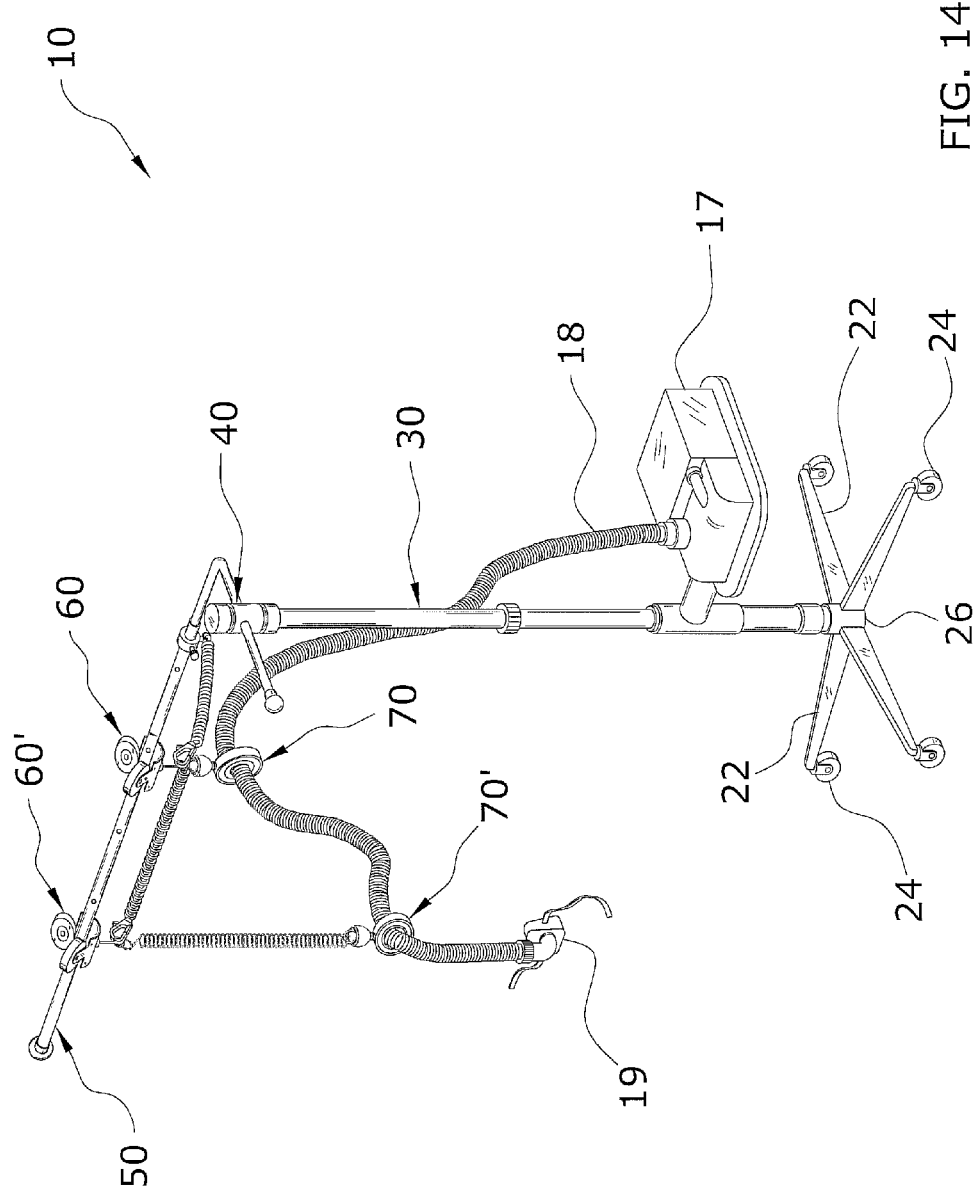
FIG. 14 is an upper perspective view of an alternate configuration of the present invention.

The base 20 of the present invention supports the present invention about or adjacent to the floor. The base 20 may be partially or wholly supported by the bed frame 12 as illustrated in FIG. 1 or the base 20 may comprised of a self-supported structure as illustrated in FIG. 14. The base 20 is also comprised of a durable and substantially strong material and configuration to withstand the weight of the present invention, CPAP device 17 and hose 18.

In a first embodiment of the base 20, the base 20 is partially supported by an adjacent bed frame 12. The base 20 includes a first platform 21 positioned about a horizontal plane and substantially coplanar with the bed frame 12. Extending from the end of the first platform 21 adjacent the bed frame 12 is a bracket 23. The bracket 23 is preferably comprised of square tubing and includes a longitudinal slot extending along the bracket 23.

Figure 13:
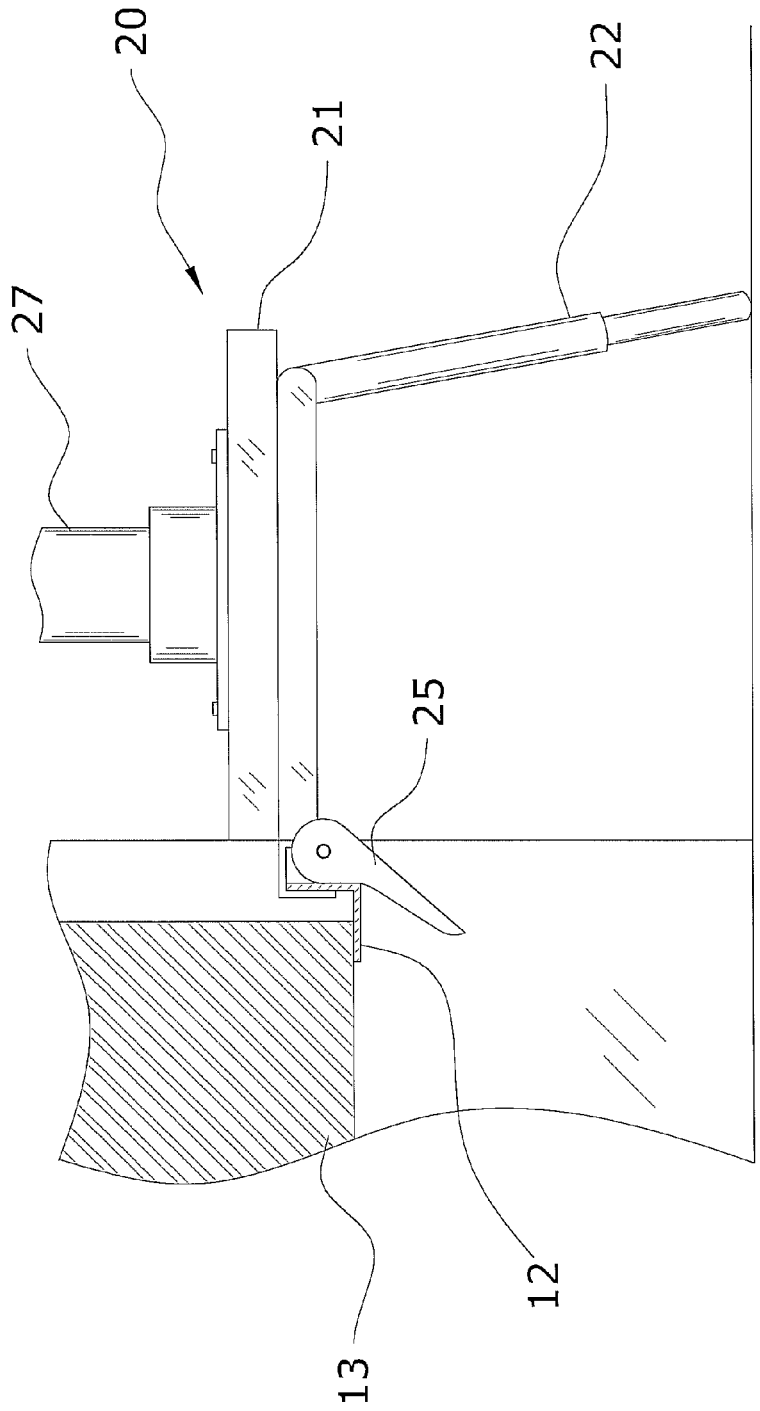
FIG. 13 is a side view of the base attached to the bed frame.

The bracket 23 attaches to the bed frame 12 by sliding the vertical edge of the bed frame 12 within the slot as illustrated in FIG. 13. The bracket 23 may also include a plurality of securing members 25 extending from the bracket 23. The securing members 25 are preferably comprised of a cam configuration and serve to secure the bracket 23 to the bed frame 12.

Extending from an opposing end of the first platform 21 as the bracket 23 is a pair of legs 22 as illustrated in FIGS. 1 and 13. The legs 22 extend perpendicular to the first platform 21 and support the opposing end of the first platform 21 as the bracket 23. The legs 22 are preferably capable of adjusting in height to allow the first platform 21 to adjust to various height bed frames 12. It is appreciated that the legs 22 may adjust in a telescoping manner or various other manners. The legs 22 may also be pivotally attached to the first platform 21 and further be spring assisted.

In a second embodiment of the base 20, the base 20 is comprised of a self-supported and movable structure. The legs 22 of the base 20 preferably radially extend outwards from a hub 26 of the present invention as illustrated in FIG. 14. Extending from and rotatably attached to each of the legs 22 opposite the hub 26 is preferably a wheel 24. The wheels 24 are preferably comprised of a castor wheel 24 configuration. The wheels 24 may also include wheel 24 locks to prevent the wheels 24 from rotating preventing the present invention from moving with respect to the floor when not desired.

C. Lower Support

Figure 2:
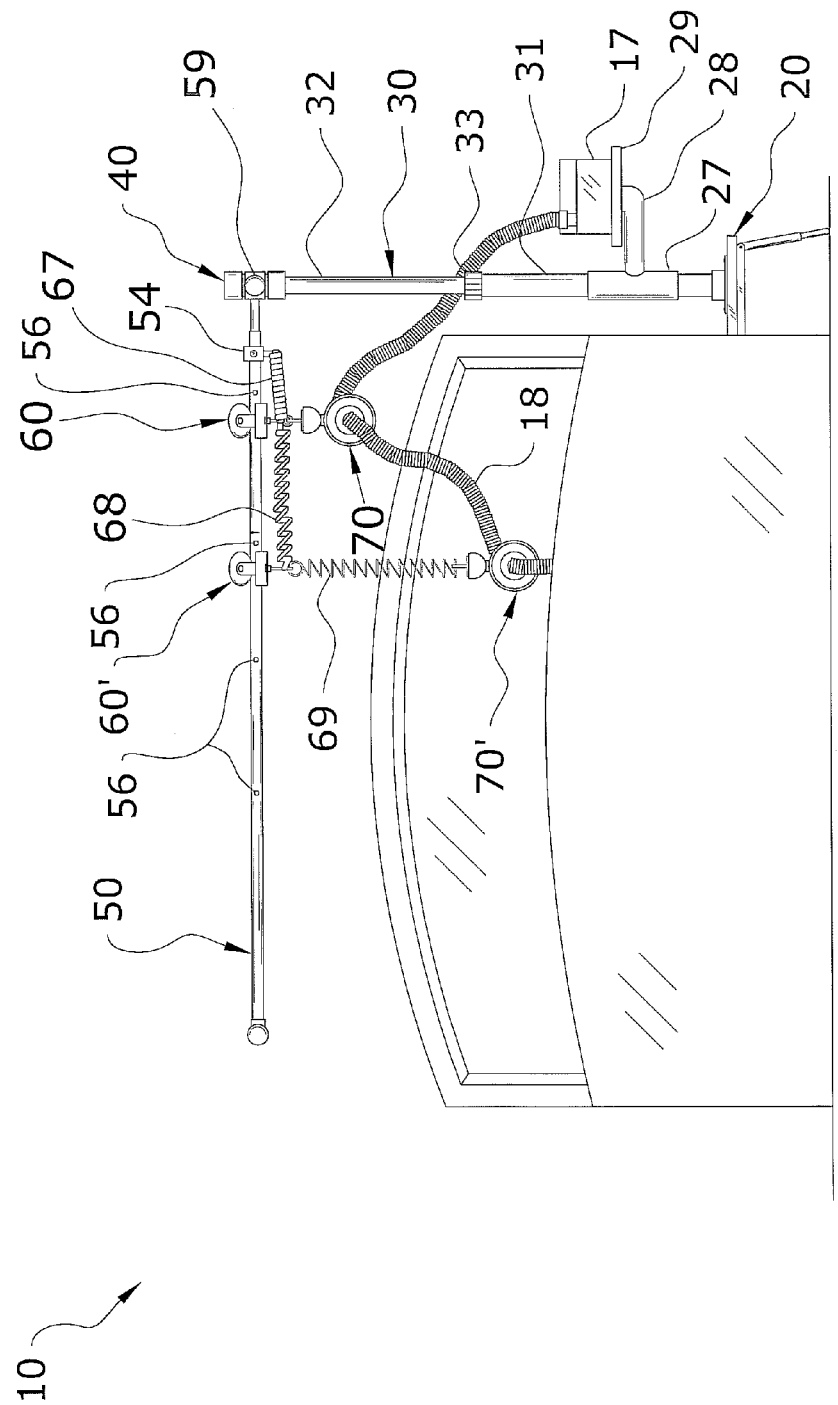
FIG. 2 is a side view of the present invention with the first elongated member and the second elongated member in a retracted position.
Figure 3:
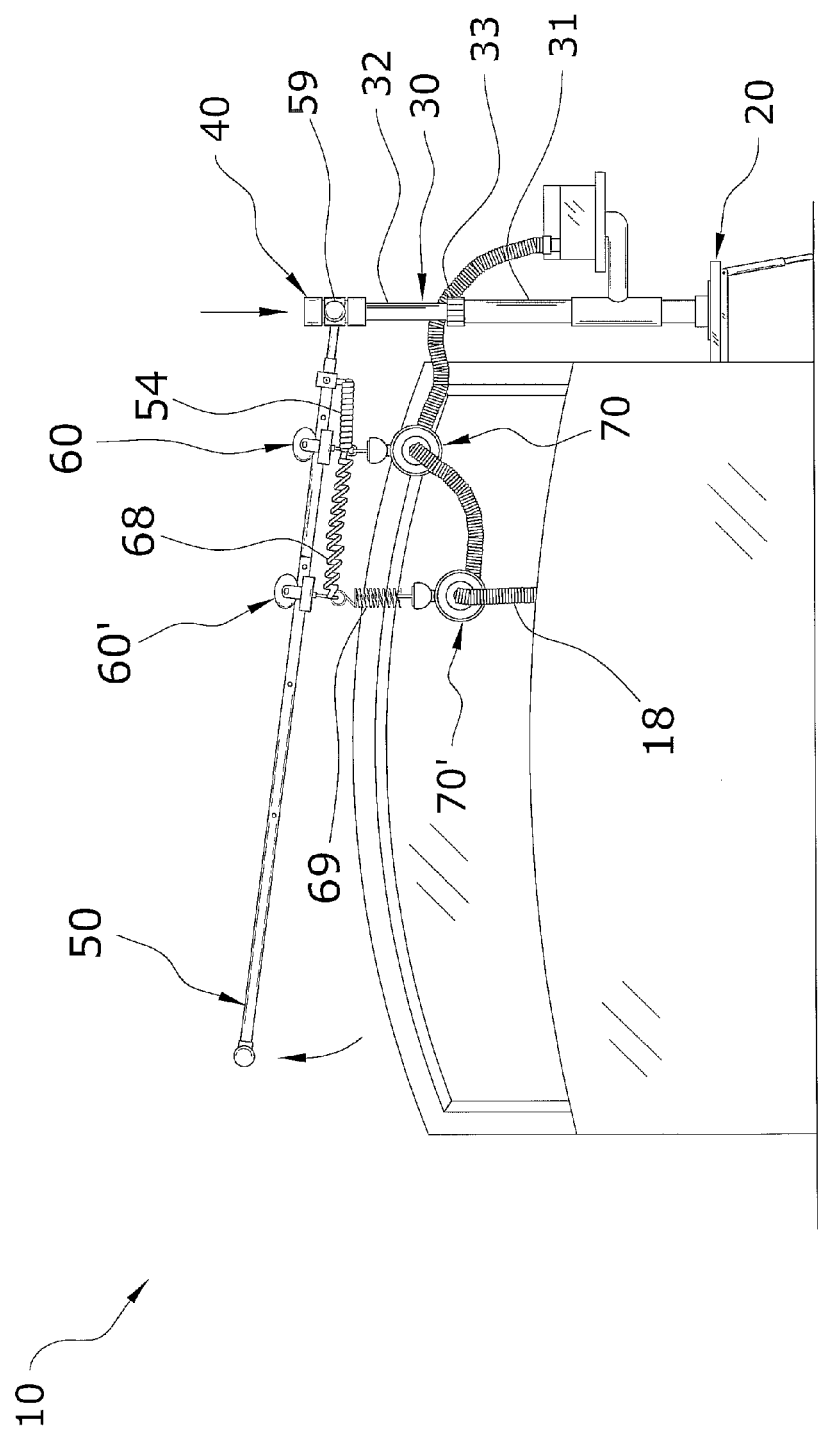
FIG. 3 is a side view of the present invention with the first elongated member and the second elongated member in a retracted position, the first horizontal support pivoted upwards and the vertical support partially retracted.

The lower support 27 extends vertically upwards from the base 20 and connects the vertical support 30 to the base 20 as illustrated in FIGS. 1 through 3. A connecting arm 28 perpendicularly extends from the lower support 27, wherein a second platform 29 preferably extends from the connecting arm 28. The second platform 29 and connecting arm 28 are preferably able to rotate around the lower support 27. The bottom end of the lower support 27 may also be weighted to assist in stabilizing the present invention.

The second platform 29 is preferably parallel to the first platform 21 and is parallel with a horizontal plane. The second platform 29 may serve as a nightstand or may also serve to support the CPAP device 17 utilized with the present invention. The second platform 29 is positionable at various heights, such as a similar height as the upper side of the mattress 13, lower side of the mattress 13 or various others.

D. Vertical Support

Extending outwardly from the lower support 27 is the vertical support 30 as illustrated in FIGS. 1 through 3. The vertical support 30 extends vertically upwards from the lower support 27 and is substantially parallel to the lower support 27. The vertical support 30 is preferably adjustable in height to accommodate for various length hoses 18, beds (i.e. bed frame 12 and mattress 13) and to better accommodate the patient 15 utilizing the present invention. It is appreciated that the vertical support 30 or lower support 27 may also be secured to the adjacent bed or wall thus alleviating the need for the base 20.

The vertical support 30 includes a first section 31 and a second section 32. The first section 31 extends from the lower support 27 and the second section 32 extends from the first section 31 opposite the lower support 27. The first section 31 and the second section 32 are preferably comprised of a tubular structure. The second section 32 also preferably is able to extend and retract from and within the first section 31 in a telescoping manner as illustrated in FIG. 3.

A connecting member 33 is also preferably attached between the second section 32 and the first section 31. By rotatably tightening the connecting member 33, the second section 32 is secured at a current height about the first section 31. By rotatably loosening the connecting member 33, the individual is able to adjust the height of the second section 32 about the first section 31.

The second section 32 also includes a plurality of adjustment openings positioned adjacent an upper end opposite the first section 31. The adjustment openings receive a pin 38, wherein the pin 38 extends through a rotator stop 36 and connects the rotator stop 36 to the second section 32 of the vertical support 30 as 14, illustrated in FIGS. 8 and 9. The adjustment openings are preferably equidistantly spaced around a perimeter of the second section 32 so the rotator stop 36 may be rotatably adjusted with respect to the second section 32 and vertical support 30. The pin 38 is also preferably spring loaded and having a twist lock via a casing 39 as to allow for easier adjustment and retention of the pin 38 and illustrated in FIG. 17.

Figure 8:
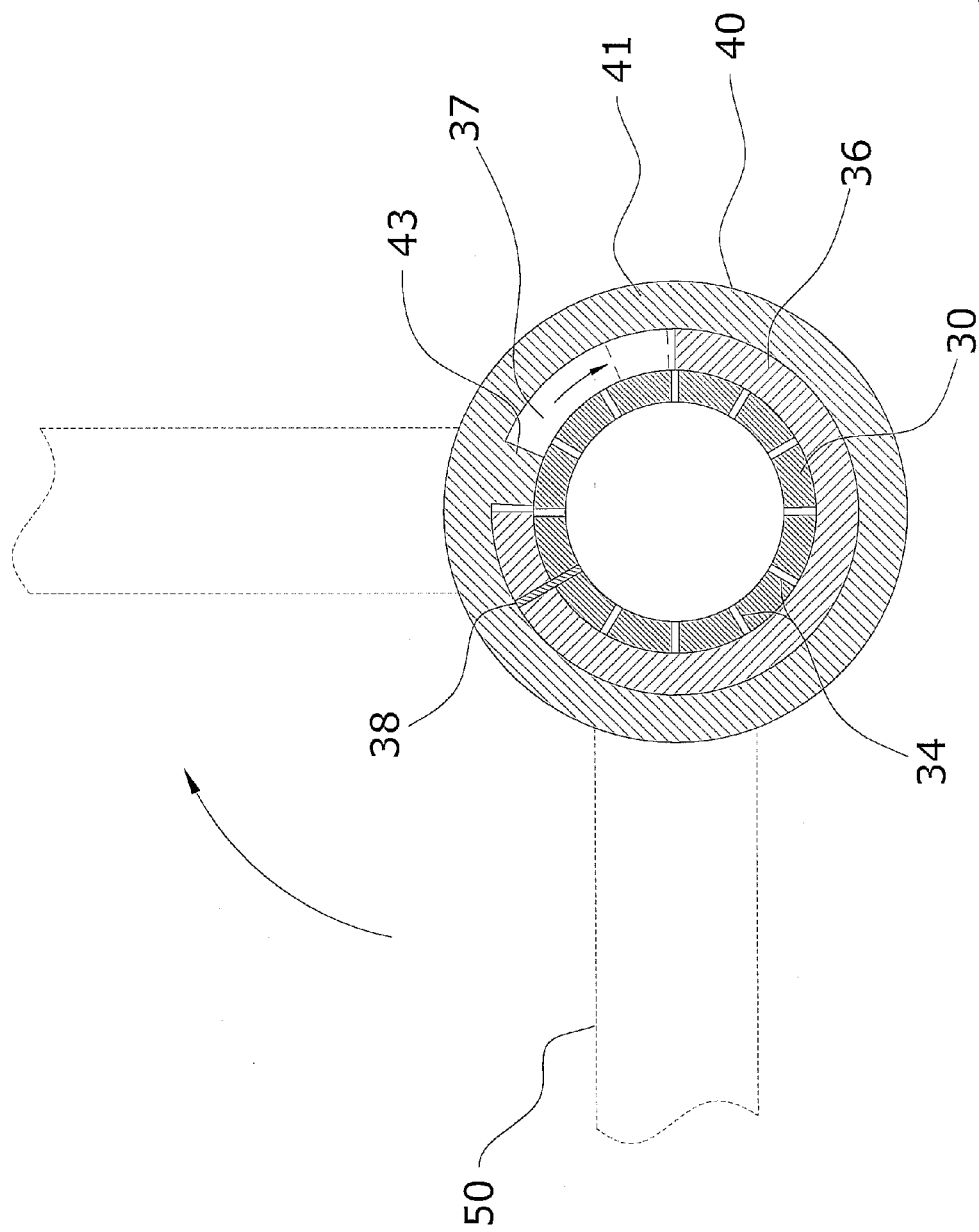
FIG. 8 is a sectional view taken along lines 8-8 of FIG. 5 and illustrating the engaging portion of the rotator assembly being adjusted by the adjusting of the gear assembly (as shown in FIG. 7), wherein the adjustment of the first horizontal support is also illustrated to show the relation of the first horizontal support to the engaging portion.
Figure 9:
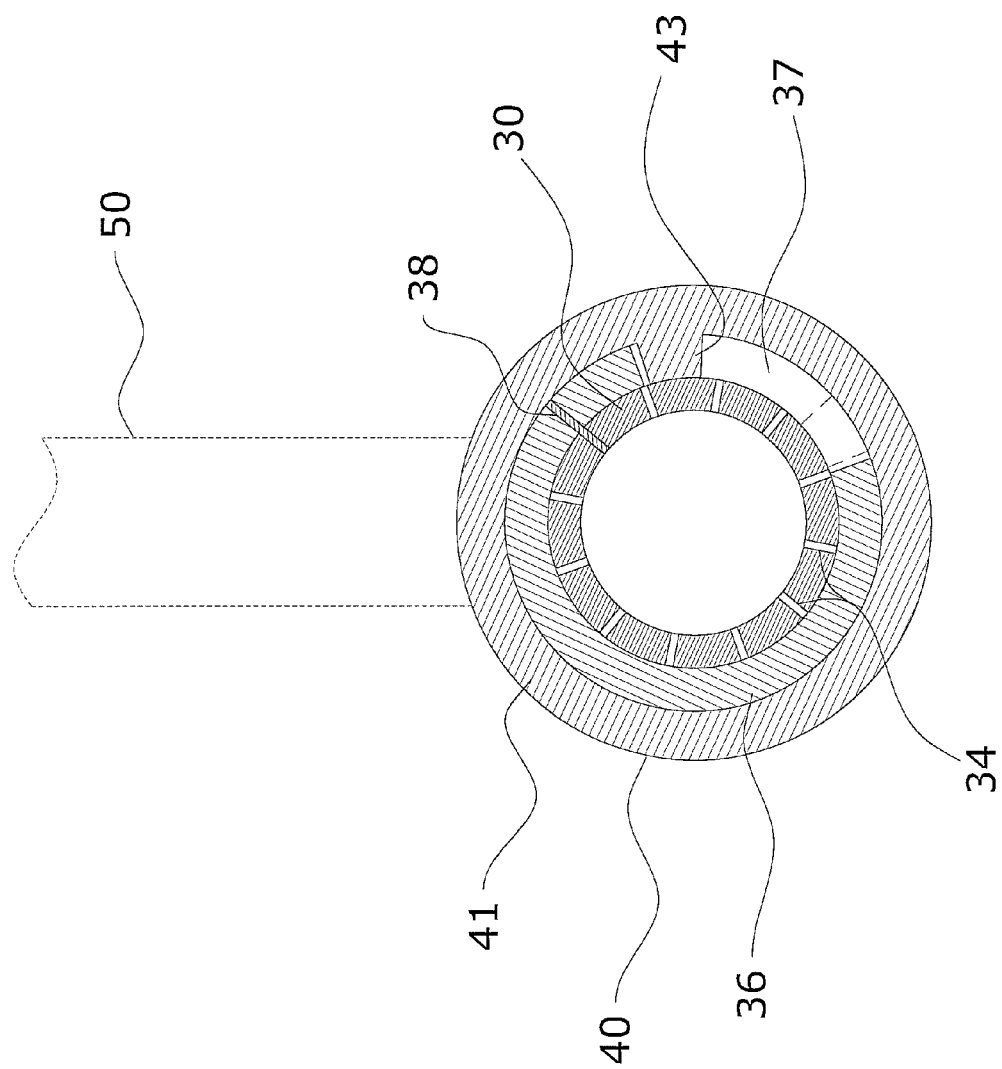
FIG. 9 is a sectional view taken along lines 9-9 of FIG. 5 and illustrating the rotator stop being adjusted around the perimeter of the vertical support to secure the engaging portion in the second initial rotating position (as shown in FIG. 7), wherein the first horizontal support is illustrated to show the relation of the first horizontal support to the engaging portion.
Figure 20:
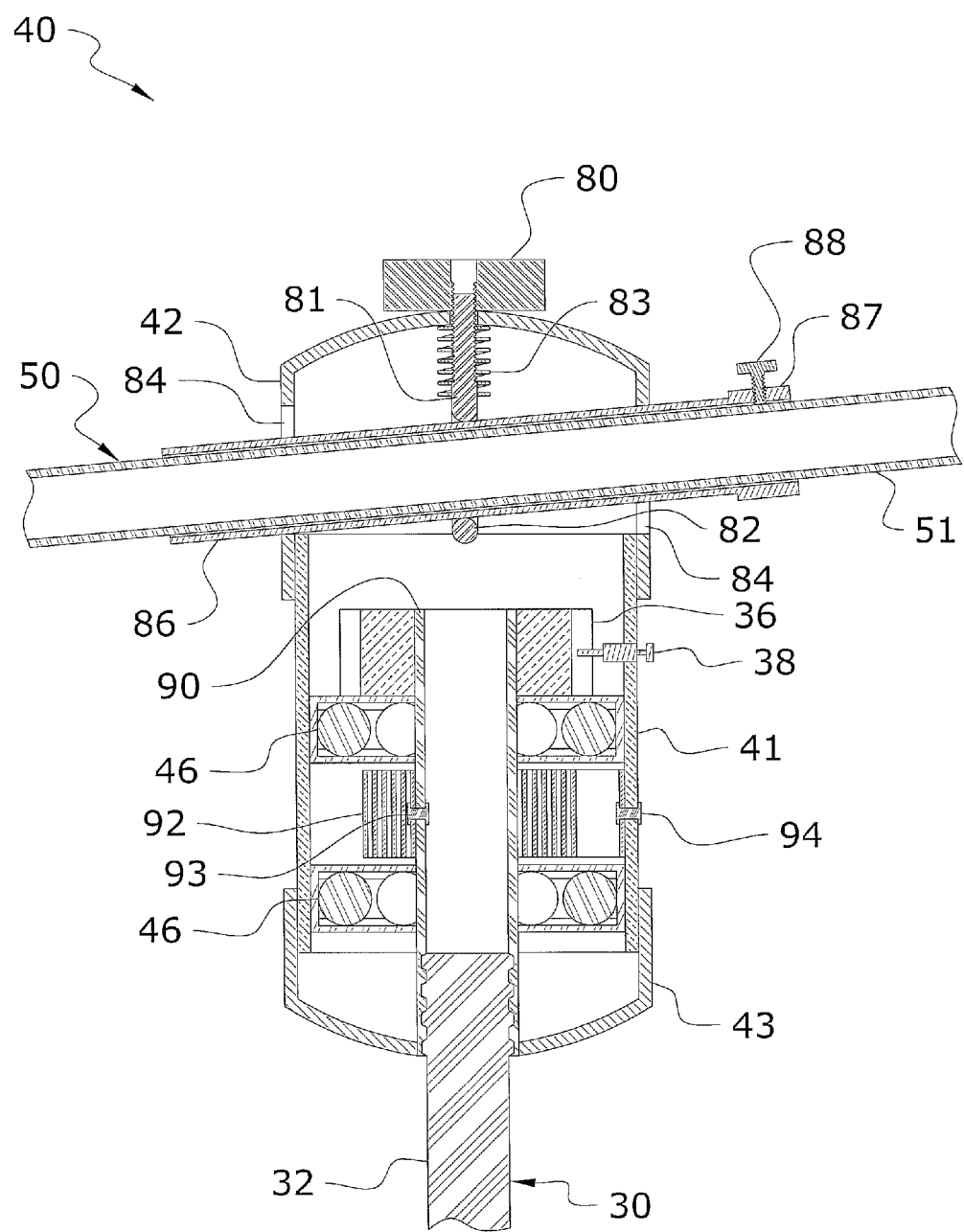
FIG. 20 is a cross-sectional view of the rotator assembly in the new embodiment.
Figure 21:
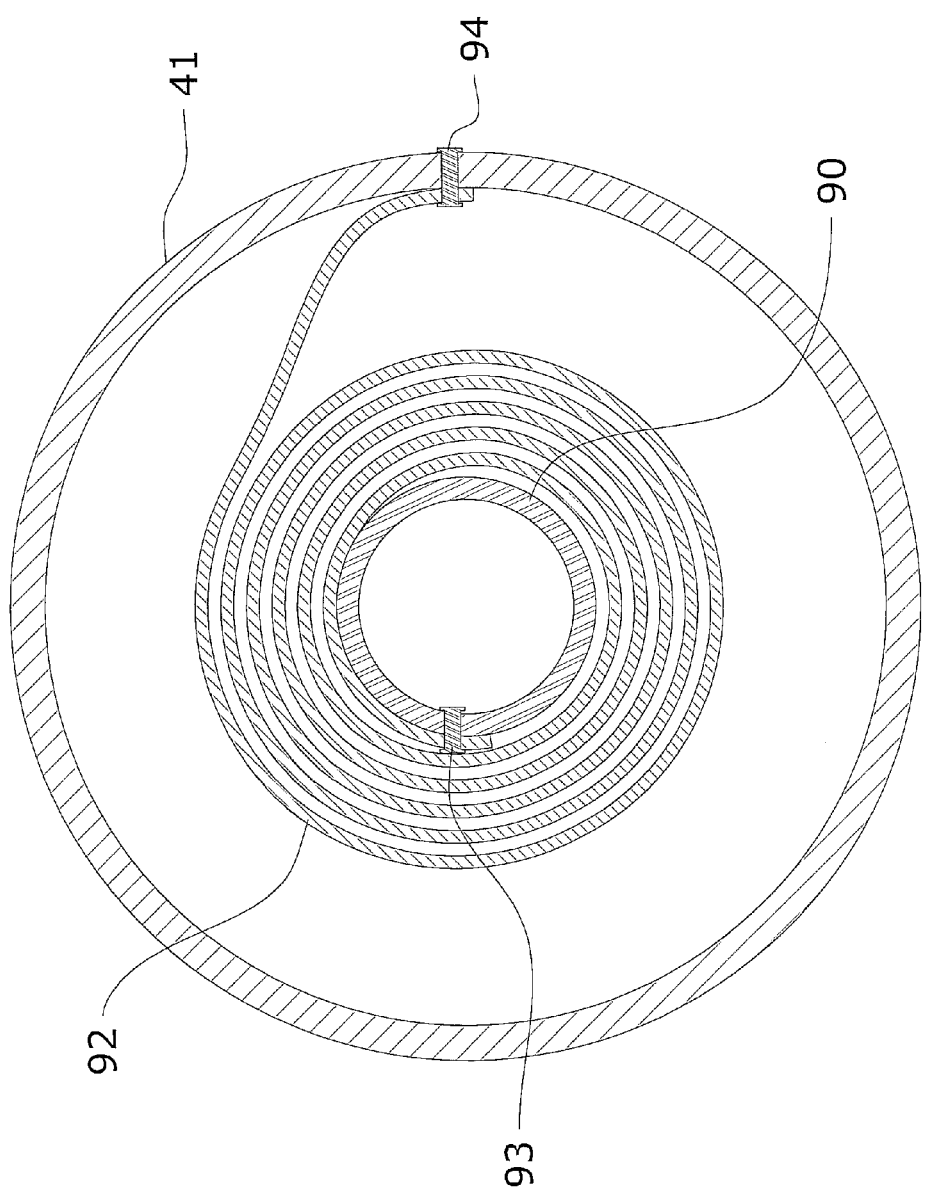
FIG. 21 is a sectional view taken along lines 21-21 of FIG. 19 illustrating the coil spring.

The rotator stop 36 is preferably comprised of a ring configuration and includes a recessed portion 37 extending along a portion of the perimeter of the rotator stop 36. The recessed portion 37 preferably extends around a quarter (i.e. 90 degrees) of the rotator stop 36 as illustrated in FIGS. 8 and 9. It is appreciated however that the recessed portion 37 may extend various lengths around the perimeter. The recessed portion 37 receives an engaging portion 43 of the rotator assembly 40, wherein the engaging portion 43 rotates around the vertical support 30 and within the recessed portion 37. The engaging portion 43 and rotator assembly 40 are thus limited in rotation distance to the length of the recessed portion 37 around the perimeter of the rotator stop 36. In the new embodiment the rotator stop 36, as illustrated in FIGS. 20 and 21, is preferably integrated with the rotator assembly 40 and will be described subsequently.

E. Rotator Assembly

Figure 4:
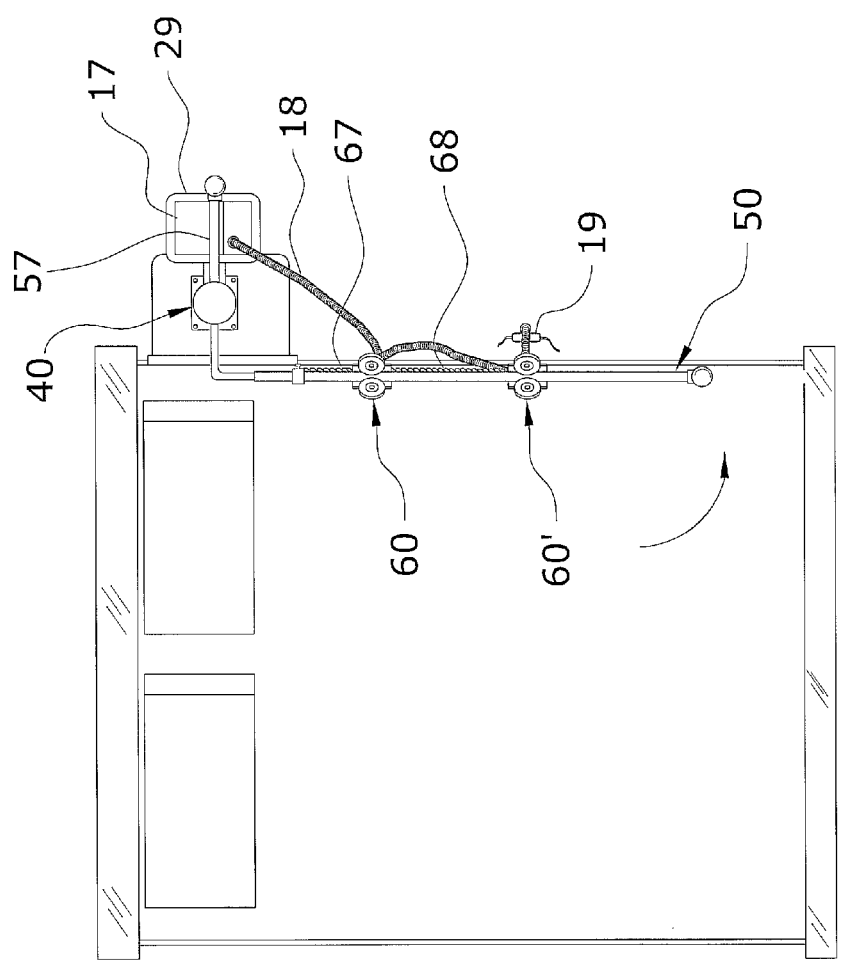
FIG. 4 is a top view of the present invention with the horizontal supports rotated to a maximum rotating position.

The rotator assembly 40 extends from the second section 32 of the vertical support 30 opposite the first section 31. The rotator assembly 40 is preferably concentric with the vertical support 30. The rotator assembly 40 allows the horizontal supports 50, 57 to rotate about the rotator assembly 40 within a substantially horizontal plane as illustrated in FIG. 4. The rotator assembly 40 accommodates the patient 15 and allow the patient 15 to move around in bed, sit up upon the bed or stand up adjacent the bed without interrupting the flow from the hose 18 to the face mask 19.

The rotator assembly 40 allows the horizontal supports 50, 57 to rotate so as to allow the horizontal supports 50, 57 to "follow" the individual as they are moving and prevent the hose 18 from becoming entangled with the individual. The rotator assembly 40 also automatically returns the horizontal supports 50, 57 to an initial rotating position after being rotated by the patient 15, wherein returning the horizontal supports 50, 57 to the initial rotating position ensures that the hose 18 remains aligned with the face mask 19. The initial rotating position is preferably when the spring 47 is decompressed a maximum amount.

Figure 5:
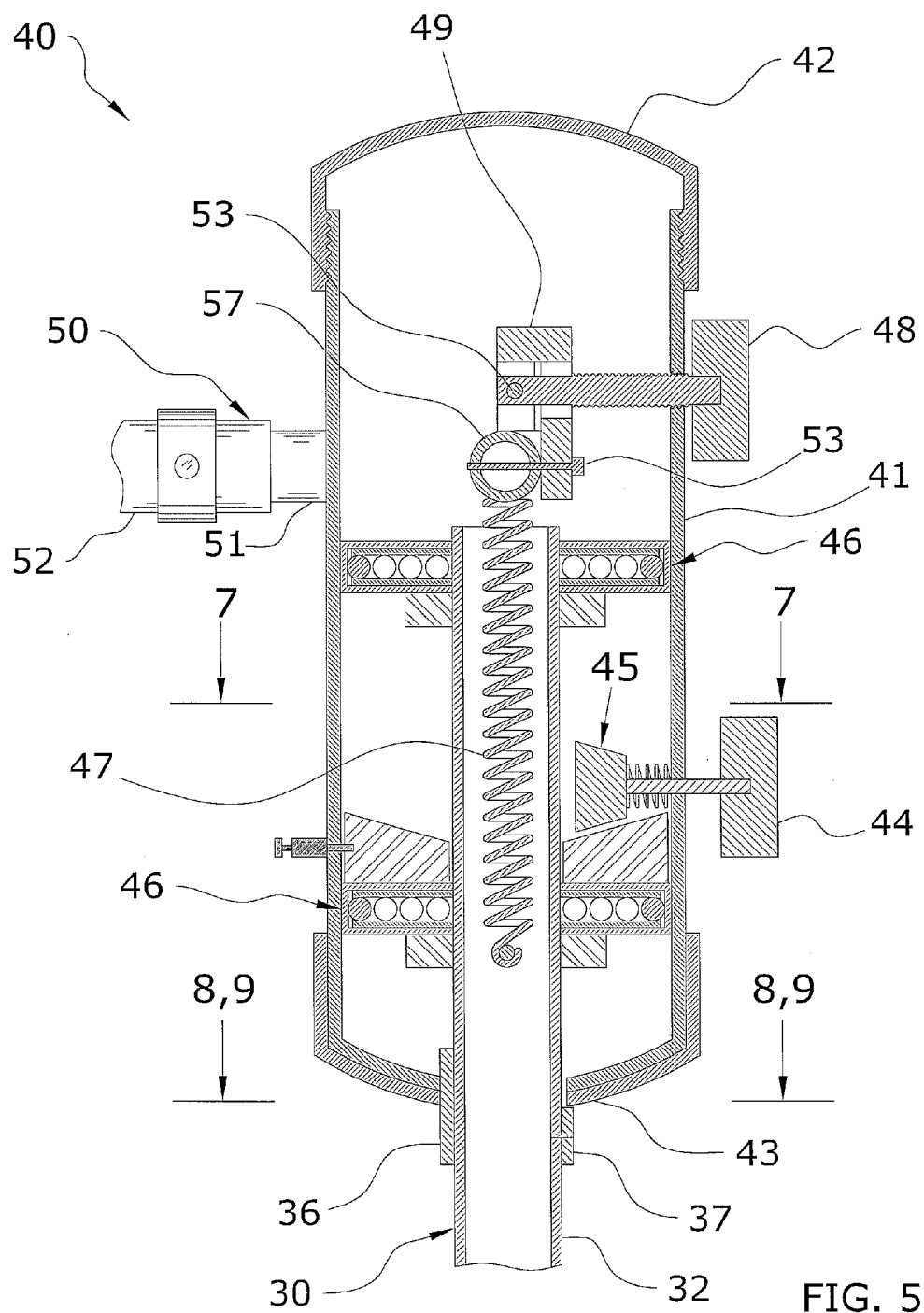
FIG. 5 is a longitudinal cross-sectional view of the rotator assembly.

The rotator assembly 40 includes an outer casing 41 to house the internal components of the rotator assembly 40 as illustrated in FIG. 5. An end cap 42 is preferably removably attached to an end of the outer casing 41 to allow a user to gain access to the internal components. The end cap 42 is preferably threadably attached to the outer casing 41; however it is appreciated that the end cap 42 may be attached in various manners.

A spring 47 also extends within the rotator assembly 40 and is attached between the inner support 51 of the first horizontal support 50 and the vertical support 30, wherein the spring 47 preferably extends within the vertical support 30 as illustrated in FIG. 5. The spring 47 is preferably comprised of a torsion spring 47. As the first horizontal support 50 and rotator assembly 40 rotate, the spring 47 tensions. When the first horizontal support 50 is released the spring 47 releases the tension and thus rotates the first horizontal support 50 and rotator assembly 40 back to the initial rotating position.

Figure 6:
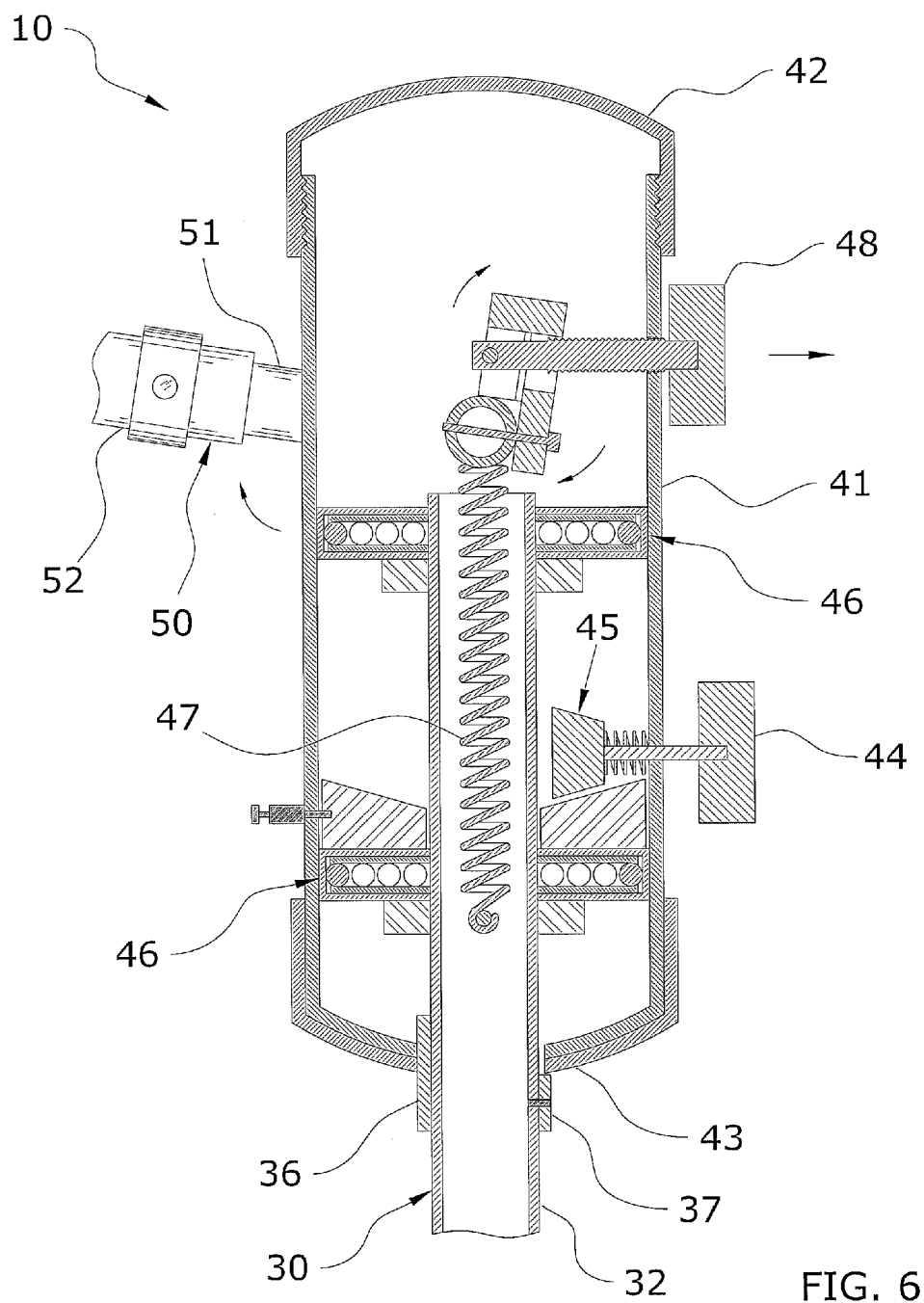
FIG. 6 is a longitudinal cross-sectional view of the rotator assembly with the second adjustment member manipulated thus causing the first horizontal support to be pivoted upwards.
Figure 7:
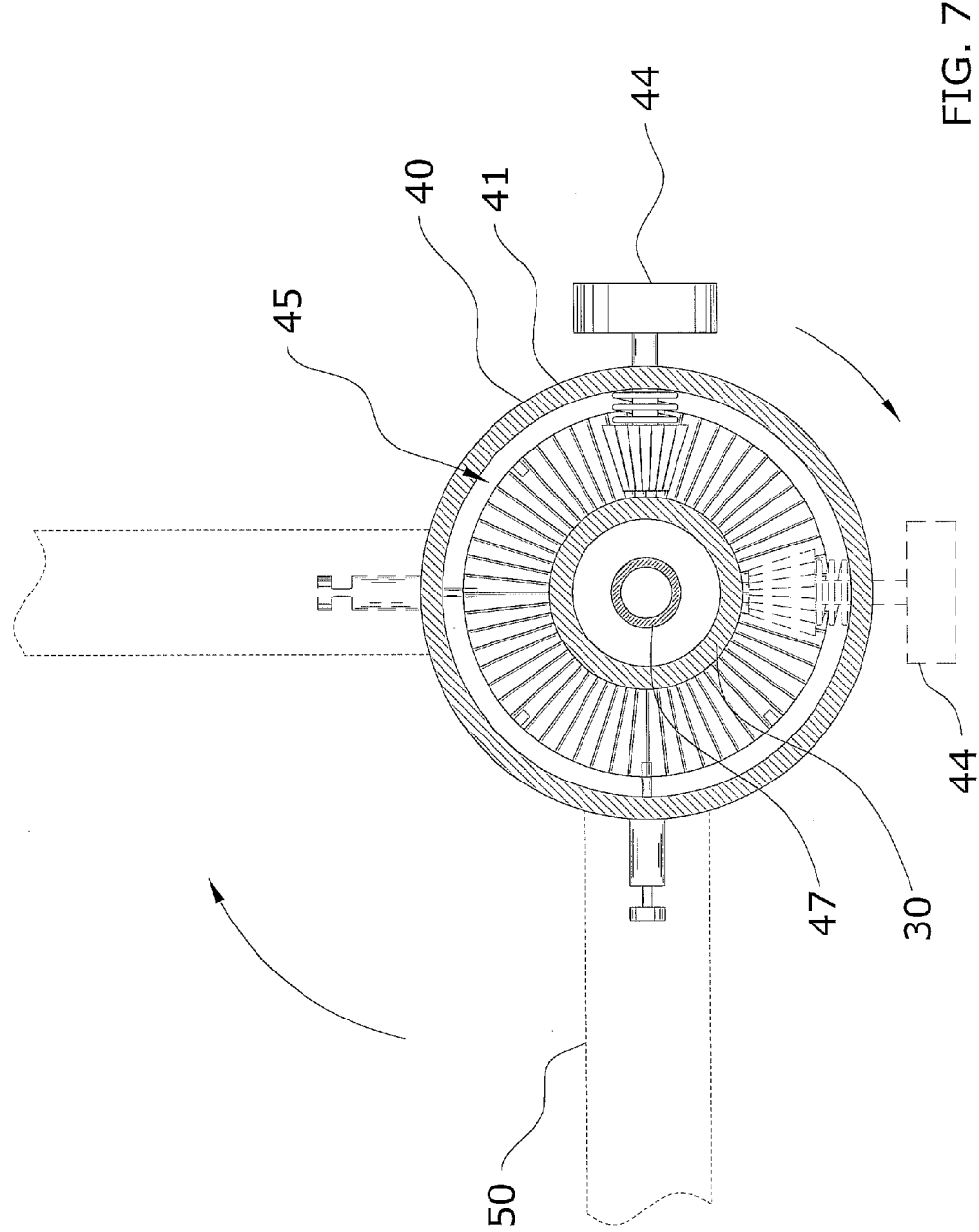
FIG. 7 is a sectional view taken along lines 7-7 of FIG. 5 and illustrating the gear assembly being adjusted thus adjusting the initial rotating position from a first initial rotating position to a second initial rotating position of the first horizontal support, wherein the adjustment of the first horizontal support is also illustrated to show the relation of the first horizontal support to the gear assembly.

A gear assembly 45 is also positioned within the rotator assembly 40 and attached to the vertical support 30. The gear assembly 45 utilized with the present invention is preferably comprised of a beveled gear configuration. By manipulating the gear assembly 45, via the first adjustment member 44, the gear assembly 45 rotates the rotator assembly 40 and the first horizontal support 50 around the vertical support 30, wherein the initial rotating position of the first horizontal support 50 is adjusted as illustrated in FIG. 7. The gear assembly 45 may also be spring loaded as illustrated in FIG. 6, wherein pulling the gear assembly 45 outward causes the gears to make contact to allow the individual to rotate the gears upon one another. Rotating the rotating assembly about the vertical support 30 also causes the spring 47 to tension, wherein the vertical support 30 is in a fixed position and the end of the spring 47 attached within the vertical support 30 is also fixed.

The gear assembly 45 also serves for the purpose of incrementally adjusting the tension of the spring 47 so that the rate of return of the horizontal support 50 could be adjusted without repositioning the horizontal support 50. It is appreciated that when the pin 38 is pulled outwards and the horizontal support 50 is in a fixed position, turning the first adjustment member 44 will increase or lessen the tension of the spring 47.

It is appreciated that the rotator stop 36 is also rotated about the vertical support 30 in a similar direction as the rotator assembly 40 and first horizontal support 50 when adjusting the initial rotating position as illustrated in FIGS. 8 and 9. The rotator stop 36 is adjusted by removing the pin 38 within the rotator stop 36 and respective adjustment opening 34 within the vertical support 30 and repositioning the rotator stop 36 about a different adjustment opening 34 of the vertical support 30.

Opposite the end cap 42 upon the casing 41, the rotator assembly 40 includes the engaging portion 43. The engaging portion 43 preferably extends toward a longitudinal center of the rotator assembly 40 and within the recessed portion 37 of the rotator stop 36. The engaging portion 43 travels within the recessed portion 37 and prevents the casing 41 and rotator assembly 40 from rotating beyond a maximum rotating position.

The horizontal supports 50, 57 are thus only able to rotate a predetermined distance away from an initial rotating position via the engaging portion 43 traveling within the recessed portion 37. The predetermined distance is preferably the perimeter length of the recessed portion 37, wherein in the preferred embodiment the predetermined distance is equal to a quarter circle or 90 degrees.

The rotator assembly 40 also includes a second adjustment member 48 to pivot the first horizontal support 50 about a vertical plane as illustrated in FIGS. 3 and 6. The second adjustment member 48 is preferably threadably attached to the outer casing 41 and extends within the casing 41. The second adjustment member 48 is also pivotally connected to a connector 49 via a fastener 53 or pin, wherein the connector 49 is connected to the first horizontal support 50 via another fastener 53 or pin.

By adjusting the first adjustment member 44 about the rotator assembly 40, the connector 49 is pivoted and thus causes the first horizontal support 50 to pivot up or down. When pivoting the first horizontal support 50 upwards, the carrier assemblies 60, 60' are able to roll back to the initial carrier position. The first adjustment member 44 and the second adjustment member 48 may be comprised of various configurations, such as but not limited to thumb screws.

The new embodiment of the rotator assembly 40 has a similar purpose as the previous embodiment in that it serves to allow the horizontal support 50 to pivot and connects the horizontal support 50 to the vertical support 30 as illustrated in FIGS. 18 through 23. The new embodiment of the rotator assembly 40 has additional improvements which will be described subsequently.

The new embodiment includes an adjustment knob 80 extending from the end cap 42 of the rotator assembly 40 to adjust the pitch of the horizontal support 50 via directly adjusting upon the inner support 51 of the horizontal support 50. The adjustment knob 80 is preferably of a threaded type and adjusts a bolt 81 vertically downward or upward via rotating the adjustment knob 50. The bolt 81 includes an eyelet 82 extending through a lower end to receive the inner support 51. As the adjustment knob 80 vertically adjusts the bolt 81, the inner support 51 is vertically adjusted thus adjusting the overall pitch of the horizontal support 50.

A tension spring 83 may also be located along the bolt 81 shaft between the eyelet 82 and the inside of the end cap 42 to secure the bolt 81 in a substantially fixed position while giving the inner support 51 a slight amount of room to move up and thus prevent easy breakage of the inner support 51. Since the bolt 81 is not threadably attached to the end cap 42, only the adjustment knob 80, the bolt 81 is able to move upwards slightly, against the force of the tension spring 83, when pressure is applied to the inner support 51.

As implied earlier, the inner support 51 extends through the rotator assembly 40 near the end cap 42 via a pair of side openings 84 extending through opposite sides of the rotator assembly 40. A sleeve member 86 also extends through the side openings 84 of the rotator assembly 40 and surrounds the inner support 51. The inner support 51 is held in a fixed horizontal position and the inner support 51 is able to slidably adjust within the sleeve member 86 to adjust the positioning of the horizontal support 50 with respect to the rotator assembly 40. One end of the sleeve member 86 may include a locking collar 87 to secure the inner support 51 in place to prevent undesired sliding within the sleeve member 86. The locking collar 87 may function in various manners, such as via threadably tightening a screw 88 against the inner support 51 when desiring to fix the inner support 51 in place and loosening the screw 87 when it is desired to slide the inner support 51 within the sleeve member 86.

Figure 23:
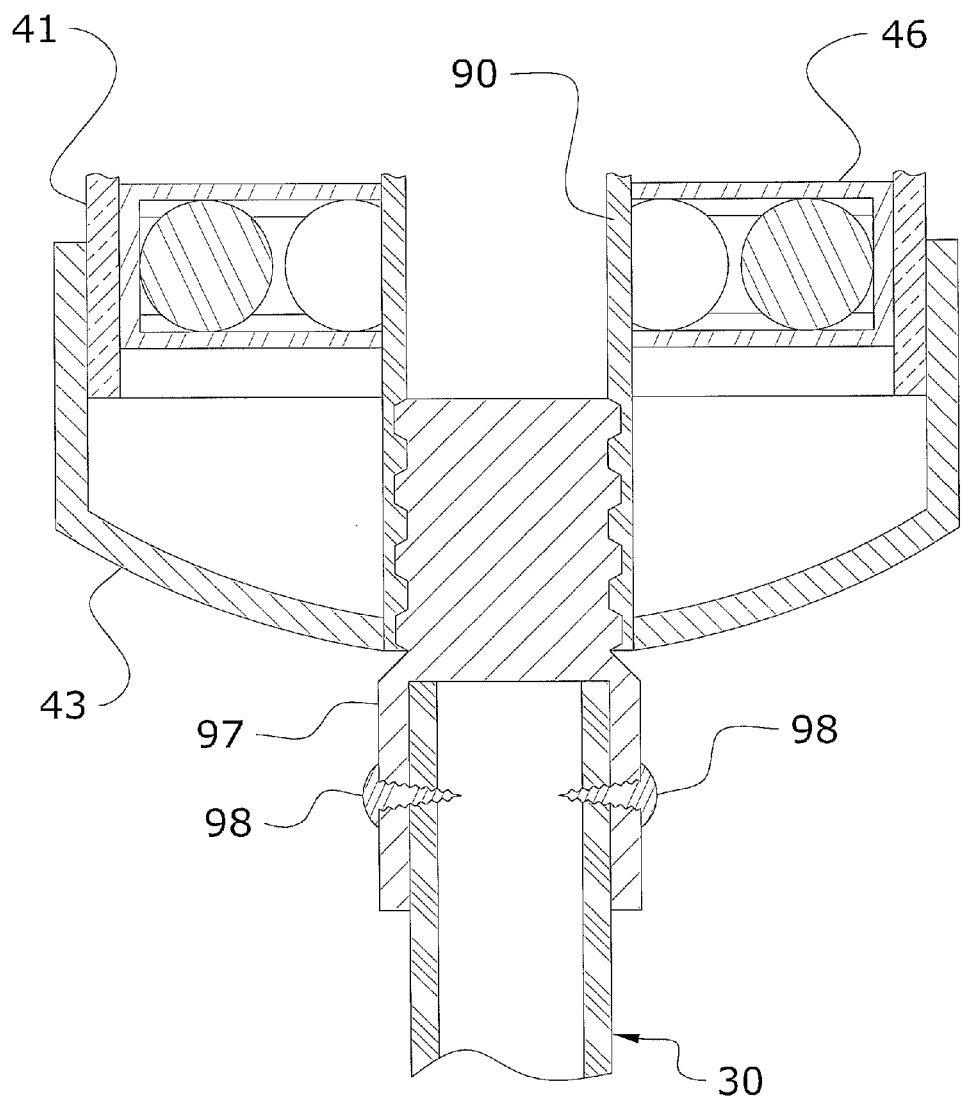
FIG. 23 is a cross-sectional view of the rotator assembly in the new embodiment including an adapter for receiving the vertical support.

The rotator assembly 40 includes an internal post 90 extending vertically upwards from the lower end of the rotator assembly 40. The internal post 90 is preferably at least partially hollow to receive the upper end of the second section 32 of the vertical post 30. The upper end of the vertical post 30 and the internal post 90 preferably threadably attach as shown in FIG. 20; however it is appreciated that an adapter 97 may be utilized to secure the vertical post 30 to the rotator assembly 40 as illustrated in FIG. 23. When using the adapter 97, the adapter 97 may be secured to the upper end of the vertical support 30 with various types of fasteners 98 as illustrated in FIG. 23. The easily removable and attachable rotator post 40 (via the threads, adapter 97, etc.) allows for the user to interchange rotator assembly 40 which may be desired such as when, but not limited to the user requires a left or right handed bed setups.

The internal post 90 extends vertically within the rotator assembly 40 in a concentric manner with the rotator assembly 40. A coil spring 92 is wound around the internal post 90 within the rotator assembly 40 so as to provide a constant force upon the rotation of the rotator assembly 40. The coil spring 92 serves the same function as the spring 47 in the previous embodiment, just in a different manner. A first end of the coil spring 92 is anchored to the internal post 90 via a first anchor 93 and a second end of the coil spring 92 is anchored to the inner surface of the outside wall of the rotator assembly 40 via a second anchor 94 as illustrated in FIGS. 20 and 21.

Figure 22:
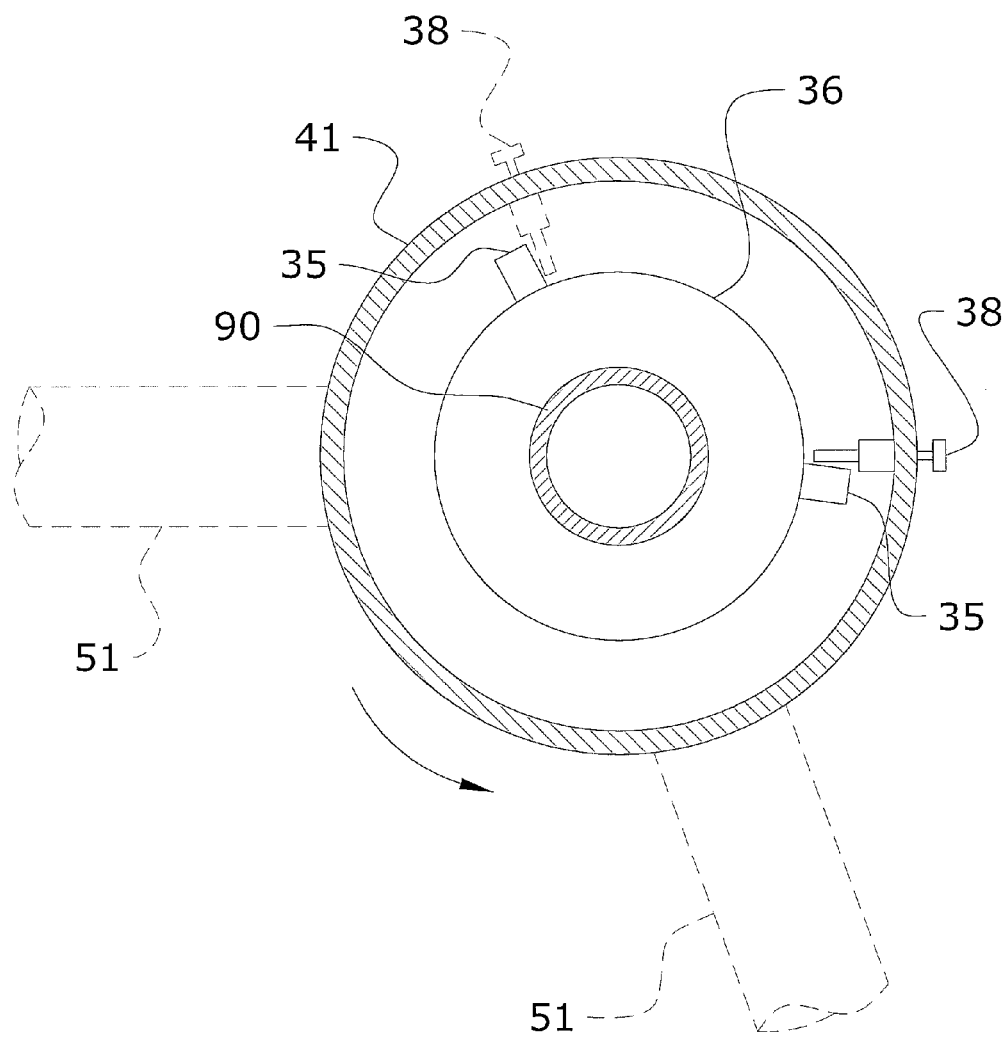
FIG. 22 is a sectional view taken along lines 22-22 of FIG. 19 showing the swing stop working to prevent the horizontal support from rotating beyond a predetermined point.

The rotator stop 36 is also preferably positioned within the rotator assembly 40 and around the internal post 90 as illustrated in FIG. 20. The rotator stop 36 is attached to the internal post 90 in a fixed manner. The rotator stop 36 includes a plurality of posts 35 extending outwardly from the rotator stop 36. The posts 35 may be arranged at various relative positions to one another depending on the amount of swing that the horizontal support is desired to have. For example, the rotator stop 36 may include two posts 35 positioned 60 degrees apart as illustrated in FIG. 22. Another example is the rotator stop 36 having three posts 35 each positioned 60 degrees apart from an adjacent post 35. A further example would be the rotator stop 36 having two posts 35 each positioned 180 degrees apart. It is appreciated that the rotator stop 36 may include a plurality of holes in which the posts 35 may be interchanged for quickly and easily changing the degree in which the horizontal support 50 is allowed to pivot.

The posts 35 serve to stop the rotation of the rotator assembly 40 and thus horizontal support 50. As the pin 38 rotates with the rotator assembly 40 it will eventually engage one of the posts 35. The pin 38 is prevented from moving past the engaged post 35 and thus the horizontal support 50 is prevented from pivoting further. The pin 38 may be able to slide partially out of the rotator assembly so as to move past the post 35. This may be accomplished through the use of a spring loaded structure as well as other configurations. As before, the rotator assembly 40 includes several bearing structures 46. In the preferred embodiment, the bearing structures 46 are located above and below the coil spring 92.

F. Horizontal Supports

The present invention includes the first horizontal support 50 extending from the rotator assembly 40. The first horizontal support 50 preferably extends perpendicular and over the mattress 13. The first horizontal support 50 also preferably extends across the mattress 13 near a front end of the mattress 13 (i.e. where the patient 15 would rest their head).

The first horizontal support 50 is preferably comprised of an elongated cylindrical shaped configuration; however it is appreciated that the first horizontal support 50 may be comprised of various configurations. The first horizontal support 50 is also preferably adjustable in length to accommodate for various size mattresses 13. The first horizontal support 50 may include longitudinally adjust in various manners, such as but not limited to in a telescoping manner. The first horizontal support 50 may also include a plurality of indicators 56 (e.g. markings, sequential numbers, sequential letters, etc.) to allow for a plurality of preset positions for the horizontal support 50 and hose supports 70, 70' according to various size mattresses 13.

The first horizontal support 50 includes an inner support 51 extending within the rotator assembly 40. The first horizontal support 50 also includes an elongated support 52 extending from the inner support 51, wherein the carrier assemblies 60, 60' preferably travel along the elongated support 52. It is appreciated that the inner support 51 and the elongated support 52 may be comprised of an integrally formed structure or separate structures.

The first horizontal support 50 also preferably includes a limiting stop 54 slidably connected to an inner end of the first horizontal support 50. The limiting stop 54 includes a fastener to extend through the limiting stop 54 and engage the horizontal support when securing the limiting stop 54 in a desired position. The limiting stop 54 prevents the carrier assemblies 60, 60' and hose supports 70, 70' from moving beyond a predetermined longitudinal position along the first horizontal support 50. It is appreciated that in an alternate embodiment, the present invention may include a first limiting stop 54 and a second limiting stop 54', wherein the carrier assembly 60, 60' is positioned between the first limiting stop 54 and the second limiting stop 54'.

The present invention also includes a second horizontal support 57 extending from the rotator assembly 40, wherein the second horizontal support 57 extends substantially over the CPAP device 17 and first platform 21. The second horizontal support 57 is preferably comprised of an elongated cylindrical shaped configuration; however it is appreciated that the second horizontal support 57 may be comprised of various configurations. A second hose support 70' extends from the second horizontal support 57 may also extend from the second horizontal support 57 in an alternate configuration of the present invention.

The first horizontal support 50 and the second horizontal support 57 may also include a first end member 55 and a second end member 59 respectively. The end members 55, 59 are preferably comprised of a ball structure. The end members 55, 59 may serve various purposes, such as places to hang the face mask 19 when not in use or to protect the patient 15 from engaging the outer portions of the horizontal supports 50, 57. In the preferred embodiment the second horizontal support 57 and the first horizontal support 50 define a 45 degree angle between thereof; however it is appreciated that the horizontal supports 50, 57 may be positioned at various angles with respect to one another.

G. Carrier Assemblies

The present invention also includes a plurality of carrier assemblies 60, 60' connected to the first horizontal support 50. The carrier assemblies 60, 60' are able to freely travel along the longitudinal axis of the first horizontal support 50 to accommodate for the individual moving while wearing the face mask 19 attached to the hose 18. The carrier assemblies 60, 60' are preferably comprised of similar configurations and include similar components.

Figure 12:
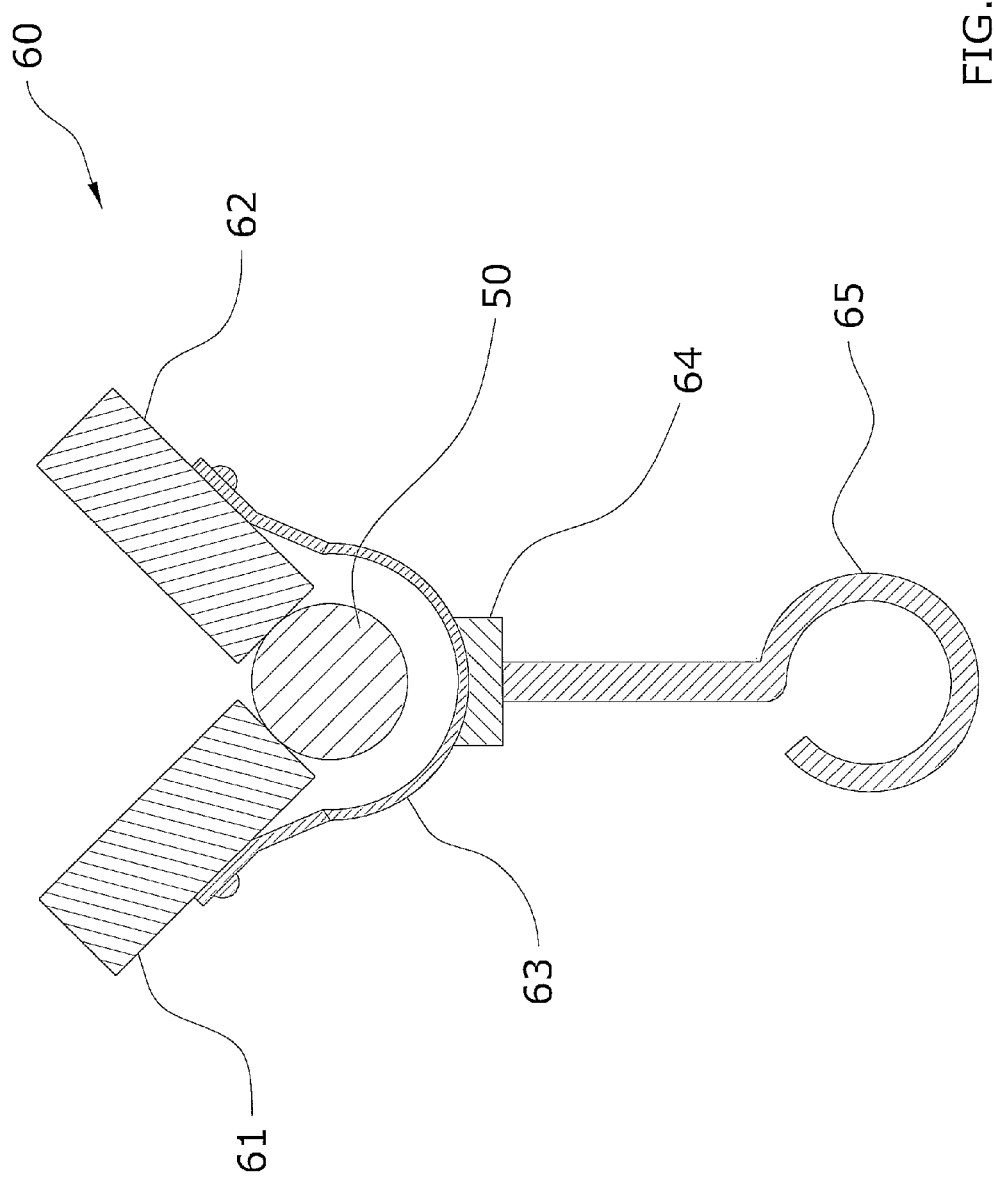
FIG. 12 is a cross-sectional view of the carrier assembly.

The carrier assembly 60, 60' includes a first roller 61 and a second roller 62. The first roller 61 and the second roller 62 are preferably perpendicular to each other and are also angled in an upper and outward manner with respect to the first horizontal support 50 as illustrated in FIG. 12.

The first roller 61 and the second roller 62 are each rotatably attached to an attachment structure 63 extending between the first roller 61 and the second roller 62 and interconnecting the first roller 61 and the second roller 62. The attachment structure 63 preferably extends around a lower side of the first horizontal support 50 to provide a downward force upon the first roller 61 and the second roller 62 and maintain connection between the rollers and the first horizontal support 50.

A central connector 64 extends from the attachment structure 63 downwardly and away from the first horizontal support 50. The central connector 64 is preferably able to rotate about the attachment structure 63. The central connector 64 is further preferably centrally positioned between the first roller 61 and the second roller 62. The central connector 64 includes a hook portion 65 to receive and connect to various elongated members 67, 68, 69 or hose supports 70, 70' of the present invention.

H. Elongated Members

The elongated members 67, 68, 69 work together to maintain the hose 18 in a desired position. The elongated members 67, 68, 69 are preferably comprised of flexible and coiled configurations to allow the first hose support 70 to extend and retract away from the first horizontal support 50. The elongated members 67, 68, 69 also help to retract the carrier assemblies 60, 60' back to an initial carrier position upon the first horizontal support 50, wherein the elongated members 67, 68, 69 retract and are pulled toward the limiting stop 54. The initial carrier position is preferably when the elongated members 67, 68, 69 are fully or substantially retracted.

Figure 15:
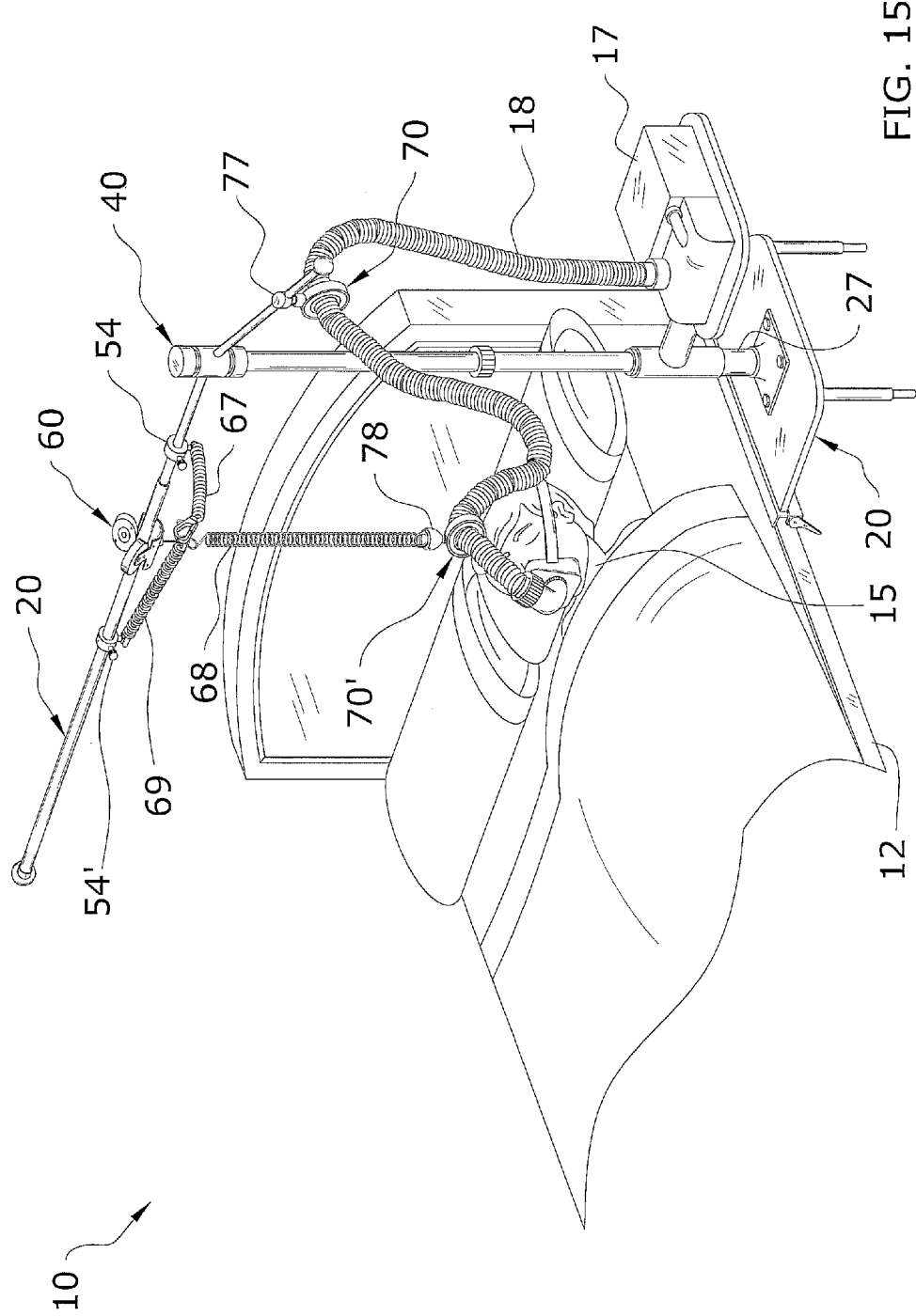
FIG. 15 is an upper perspective view of another alternate configuration of the present invention.
Figure 16:
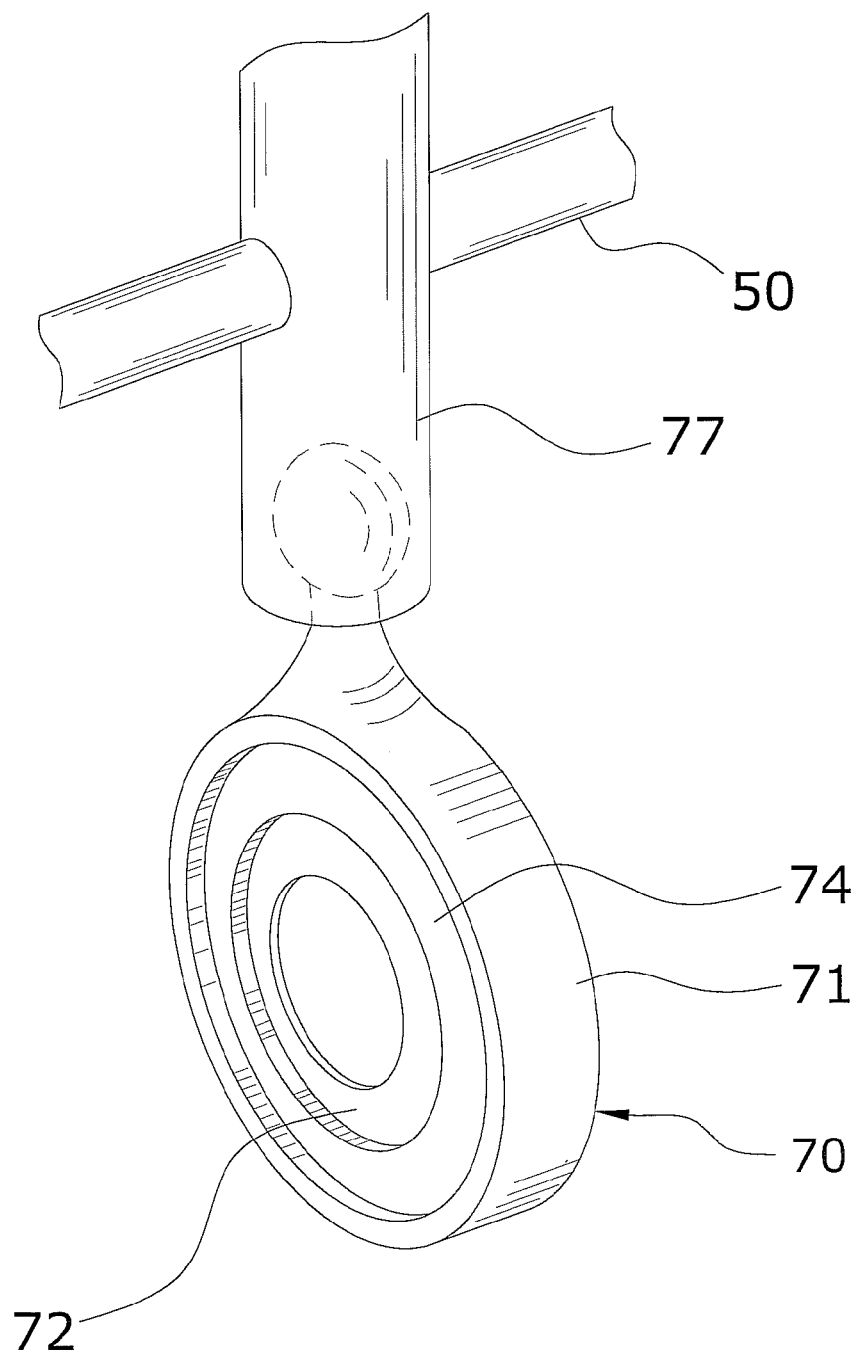
FIG. 16 is an upper perspective view of the hose support including a swivel connecting structure.
Figure 17:
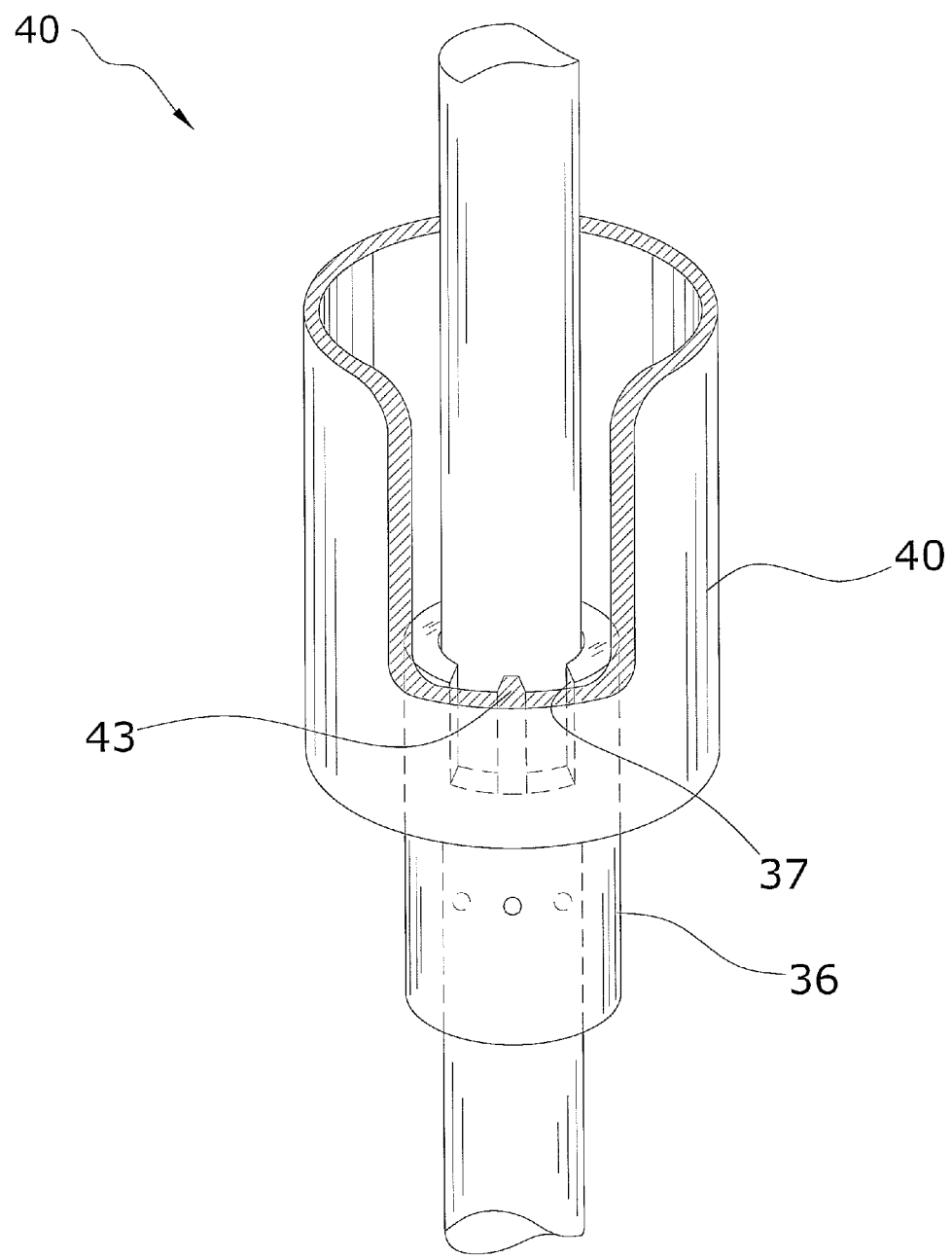
FIG. 17 is a cutaway upper perspective view illustrating the connection of the rotator stop to the rotator assembly.

A first elongated member 67 preferably extends between the first limiting stop 54 and the first carrier assembly 60. A second elongated member 68 preferably extends between the first carrier assembly 60 and the second carrier assembly 60'. A third elongated member 69 further extends between the second carrier assembly 60' and the second hose support 70'. In the alternate configuration of the present invention, the limiting stops 54 are positioned upon the first horizontal support 50 so that when either the first or second elongated member 68 tensions, the opposing second or first elongated member 67 collapses in an equalizing manner as illustrated in FIG. 15.

Figure 18:
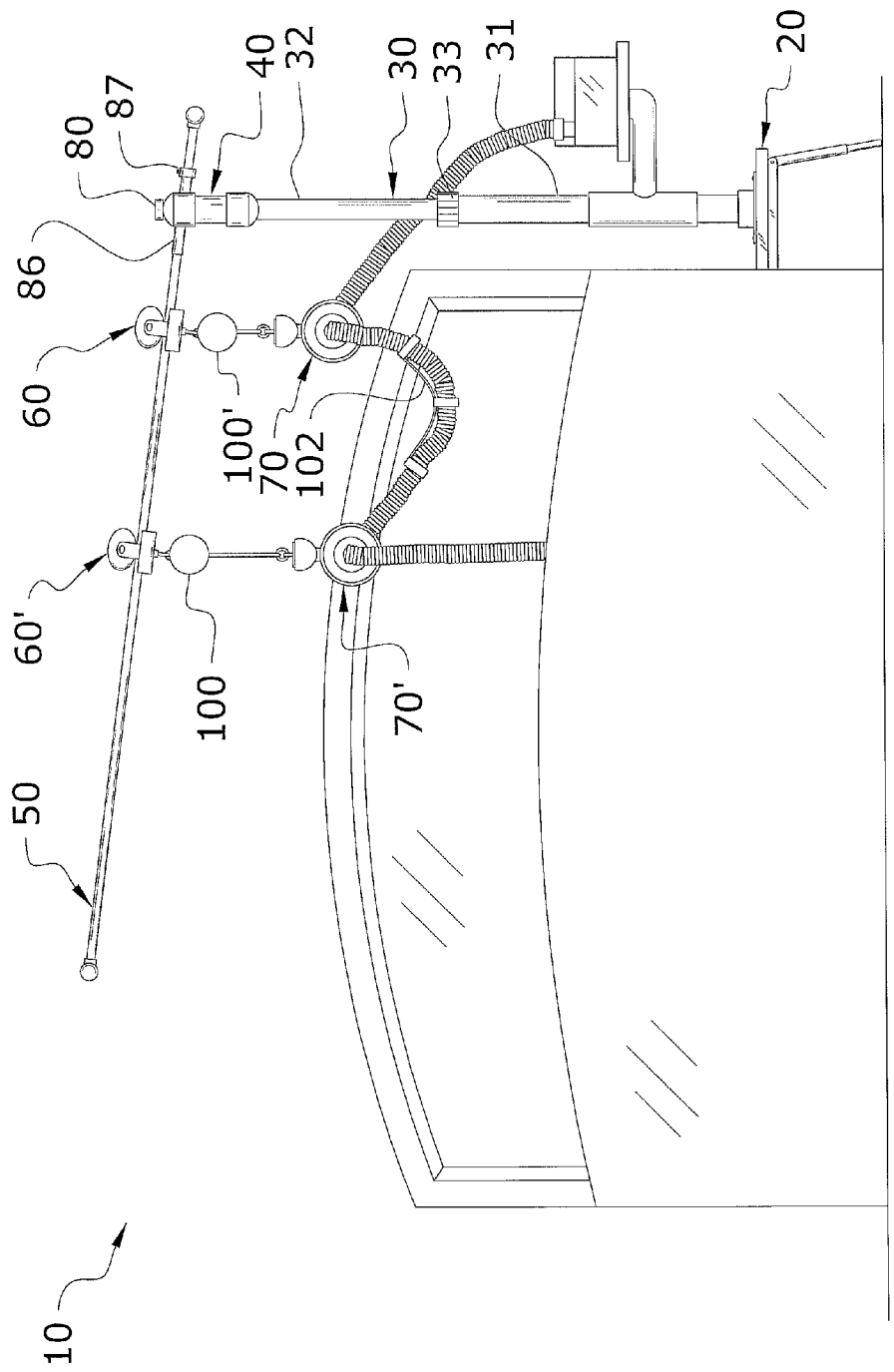
FIG. 18 is a front view of the new embodiment of the present invention.
Figure 19:
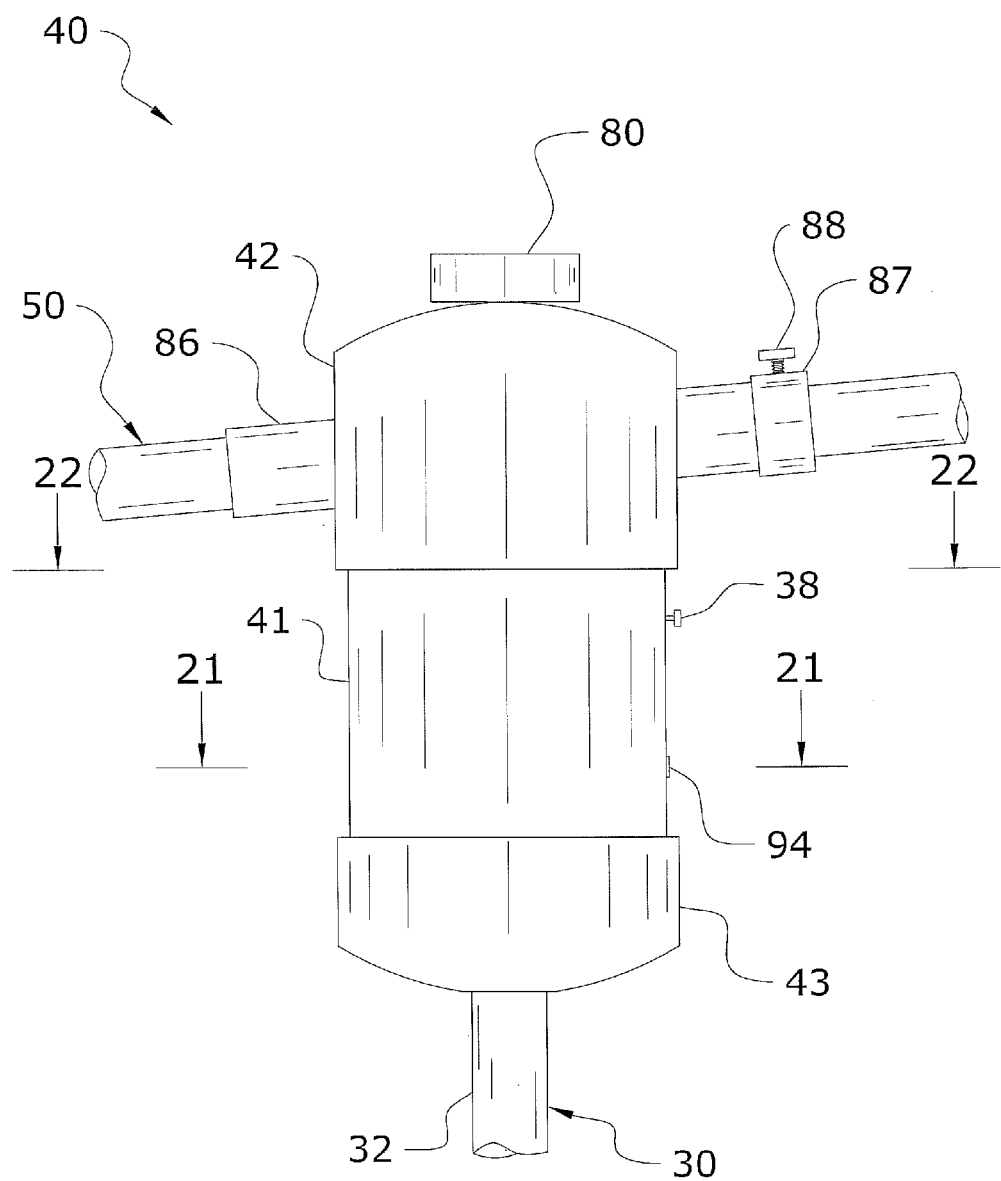
FIG. 19 is a front view of the rotator assembly in the new embodiment.

In the new embodiment, a retractable device 100, 100' preferably extends from each of the carries 60, 60' as illustrated in FIG. 18. The retractable device 100, 100' is spring loaded and includes a wire or other elongated element that extends and retracts with the hose 18. A return spring 102 may also be located along the hose 18 between each of the retractable devices 100, 100'. The return spring 102 is affixed to the hose 18 and serves to keep the hose 18 in a compact position when not being stretched by the user. The return spring 102 is preferably comprised of a tempered flat spring configuration. The return spring 102 also helps in returning the carrier assemblies 60, 60' to an initial position.

I. Hose Supports

The present invention includes a plurality of hose supports 70, 70' mechanically connected to the first horizontal support 50 for supporting the hose 18 at various positions. The present invention preferably includes a first hose support 70 and a second hose support 70' extending from and mechanically connected to the first horizontal support 50 as illustrated in FIG. 1.

The hose supports 70, 70' are comprised of substantially similar configurations. The hose supports 70, 70' allow the hose 18 to be pulled through the hose supports 70, 70' and extended towards the individual. The hose supports 70, 70' also secure the hose 18 from being extended or retracted from the hose supports 70, 70' when not being pulled or pushed upon. The first hose support 70 is preferably positioned to receive the hose 18 at a substantially uppermost portion of the hose 18. The second hose support 70' is preferably positioned to receive the hose 18 adjacent the end of hose 18 and face mask 19.

The first hose support 70 is attached to the first horizontal support 50 via the first connecting structure 77 and the second hose support 70' is attached to the third elongated member 69 via a second connecting structure 78. The connecting structures 77, 78 preferably allow the hose supports 70, 70' to rotate in a universal manner. The connecting structures 77, 78 also preferably each include bearing structures 46 to allow the connecting structures 77, 78 to rotate in a smooth manner. The hose supports 70, 70' are able to slidably adjust about the first horizontal support 50 via the respective carrier assemblies 60, 60'. The connecting structures 77, 78 are further preferably comprised of a 360 degree universal ball joint configuration.

Figure 10:
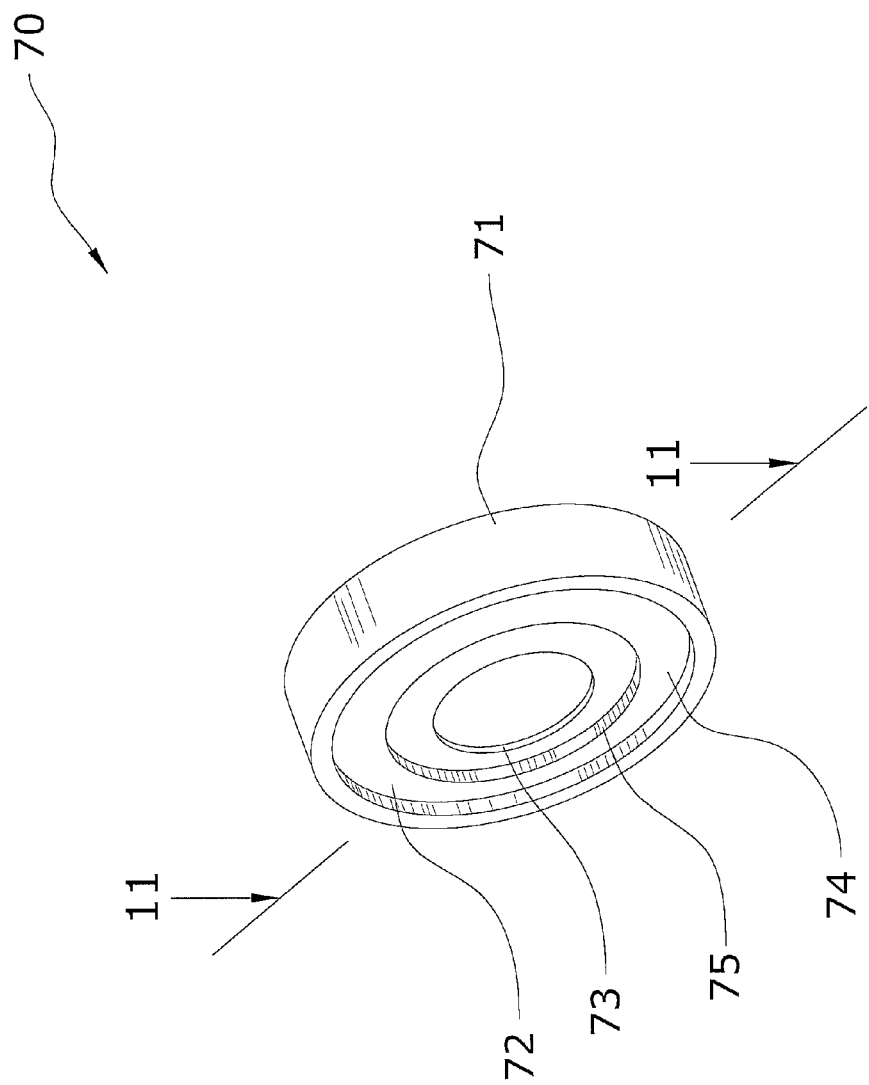
FIG. 10 is an upper perspective view of the hose support.
Figure 11:
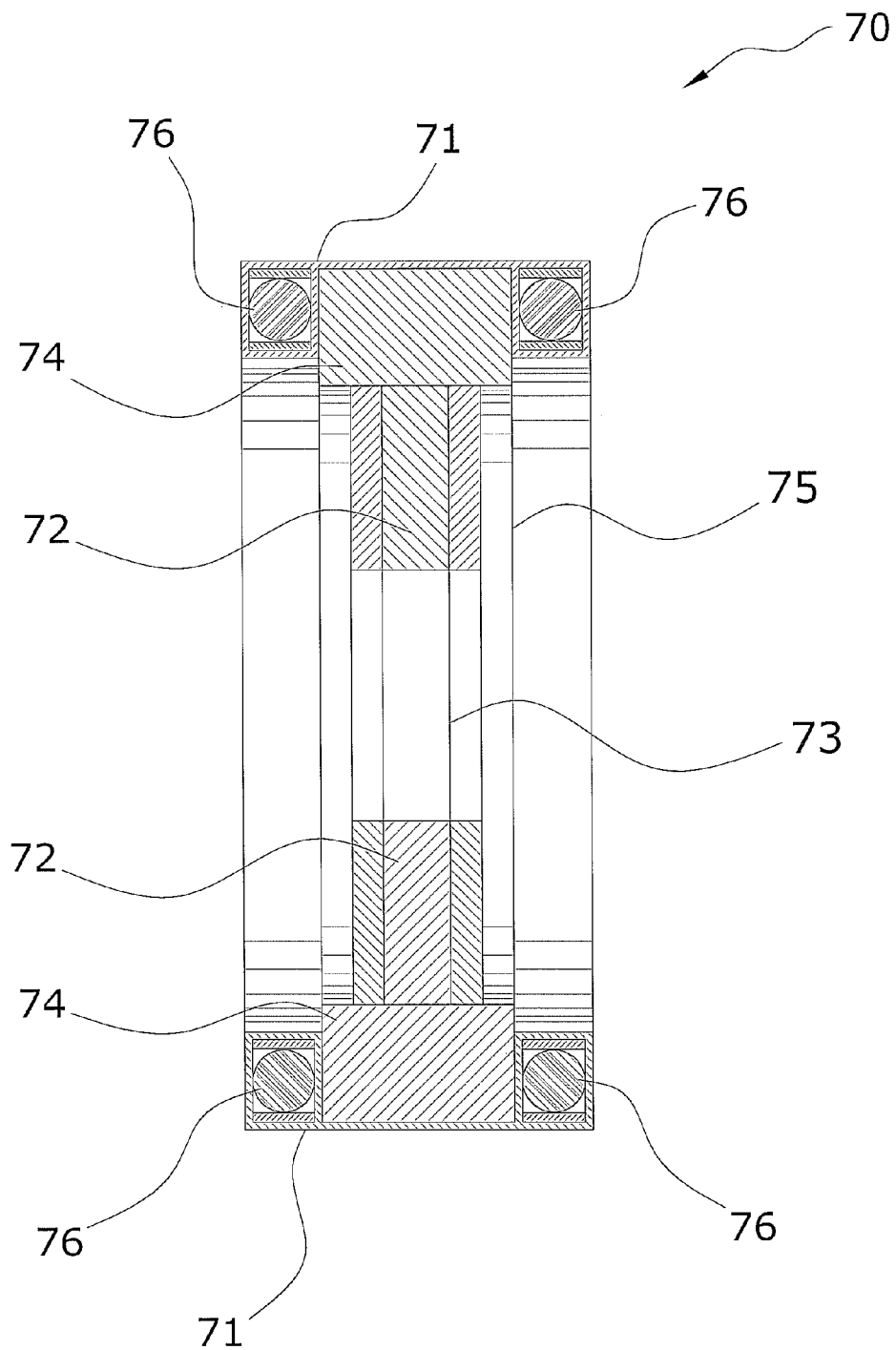
FIG. 11 is a sectional view taken along lines 11-11 of FIG. 10

The hose support 70 includes an outer ring 71, a pair of outer discs 74 extending within the outer ring 71, a bearing structures 76 positioned between the outer discs 74 and the inner ring 71 and a flexible and resilient membrane 72 extending within the inner ring 71 and sandwiched between the outer discs 74 as illustrated in FIGS. 10 and 11. A first opening 73 extends through the membrane 72 and a second opening 75 extends through the outer discs 74. A diameter of the first opening 73 is substantially smaller than a diameter of the second opening 75 and is further similar to the hose 18 diameter.

The hose 18 extends through the first opening 73 of the membrane 72 and the membrane 72 is able to flex within the second opening 75 of the outer discs 74. The outer discs 74 are preferably comprised of a rigid structure to maintain the outer perimeter of the membrane 72 in a fixed position and thus allow the membrane 72 to better secure the hose 18 within the first opening 73. In the alternate configuration of the present invention, the first hose support 70 is attached to the second horizontal support 57 via the first connecting structure 77. The bearing structure 76 of the hose support 70 allows the member 72 of the hose support 70 to rotate to prevent twisting of the hose 18.

J. Operation of Preferred Embodiment

In use, the hose 18 is first attached to the face mask 19, wherein the face mask 19 may include a 360 degree swivel. The opposing end of the hose 18 is now extended through the second hose support 70'. The hose 18 is now extended through the first hose support 70 and subsequently attached to the CPAP device 17. The hose 18 is adjusted with respect to the hose supports 70, 70' so that the hose 18 is adequately positioned lengthwise within the hose supports 70, 70' to allow the user to move around comfortably while lying on the mattress 13 and wearing the face mask 19.

The initial rotating position and initial pivoting position may also be adjusted to conform to the user and the bed being utilized. It is appreciated that the height of the vertical support 30 and the length of the first horizontal support 50 may also need to be adjusted to more properly accommodate the user. The user is now able to move around freely in bed without entangling the hose 18 or being restricted by the hose 18.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:
1. A breathing hose support system comprising:
   a vertical support; a rotator assembly extending from said vertical support; wherein said rotary assembly includes a spring to provide a constant rotational force upon said rotary assembly; wherein said rotator assembly includes a rotator stop to limit a degree of rotation of said rotator assembly; a horizontal support extending from said rotator assembly, wherein said horizontal support pivots with a rotation of said rotary assembly; and at least one hose support extending from said horizontal support including a plurality of carrier assemblies movably connected along said horizontal support.

2. A breathing hose support system comprising:
a vertical support;
a rotator assembly extending from said vertical support;
wherein said rotary assembly includes a spring to provide a constant rotational force upon said rotary assembly; wherein said rotator assembly includes a rotator stop to limit a degree of rotation of said rotator assembly;
a horizontal support extending from said rotator assembly, wherein said horizontal support pivots with a rotation of said rotator assembly; at least one hose support extending from said horizontal support including a plurality of carrier assemblies movably connected along said horizontal support and a return spring to return said plurality of carrier assemblies to an initial position.

3. A breathing hose support system, comprising:
a vertical support; a rotator assembly extending from said vertical support, wherein said rotator assembly rotates with respect to said vertical support; a horizontal support extending from said rotator assembly wherein said horizontal support pivots with a rotation of said rotator assembly; an adjustment knob extending from said rotator assembly to engage said horizontal support, wherein manipulation of said adjustment knob adjusts a pitch of said horizontal support; and at least one hose support extending from said horizontal support to support a breathing hose.

4. A breathing hose support system comprising:
a base;
a vertical support;
a rotator assembly concentrically mounted on said vertical support opposite said base and including a rotator stop, wherein said rotator stop limits a rotation of said rotator assembly;
at least one horizontal support extending from said rotator assembly, wherein said at least one horizontal support rotates concentrically about said vertical support via said rotator assembly and pivots in a vertical direction; and
at least one hose support extending from said horizontal support wherein said at least one hose support includes a flexible membrane having at least one opening.

5. A breathing hose support system comprising:
a base; a vertical support; a rotator assembly concentrically mounted on said vertical support opposite said base and including a rotator stop, wherein said rotator stop limits a rotation of said rotary assembly; at least one horizontal support extending from said rotator assembly, wherein said at least one horizontal support rotates concentrically about said vertical support via said rotator assembly and pivots in a vertical direction; and
a least one hose support extending from said horizontal support; wherein said at least one hose support is swivelly connected with respect to said at least one horizontal support.

6. A breathing hose support system, comprising:
a vertical support;
at least one horizontal support extending from said vertical support; means for rotating said at least one horizontal support concentrically about said vertical support; means for pivotally adjusting said horizontal support within a vertical plane; at least one carrier assembly movably connected to said at least one horizontal support, wherein said at least one carrier assembly travels along a longitudinal axis of said at least one horizontal support; and at least one hose support extending from said at least one carrier assembly.

7. The breathing hose support system of claim 6, wherein said at least one carrier assembly includes a first roller and a second roller, wherein said first roller is substantially perpendicular to said second roller.

8. The breathing hose support system of claim 6 including a flexible elongated member mechanically connected between said at least one carrier assembly and at least one horizontal support.

9. The breathing hose support system of claim 8, wherein said flexible elongated member returns said at least one carrier assembly to an initial carrier position.

* * * * *